United States Patent [19]
Knodel et al.

[11] Patent Number: 6,086,606
[45] Date of Patent: *Jul. 11, 2000

[54] MANUALLY-OPERABLE SURGICAL TOOL SUITABLE FOR LAPAROSCOPIC OPERATIONS, READILY ADAPTABLE FOR DIFFERENT FUNCTIONS BY QUICK CHANGE OF TISSUE-CONTACTING OPERATIONAL ELEMENTS

[76] Inventors: Bryan D. Knodel, 6100 N. Country Club, Flagstaff, Ariz. 86004; John A. Williams, 1007 N. Revere St., Mesa, Ariz. 85201

[*] Notice: This patent issued on a continued prosecution application filed under 37 CFR 1.53(d), and is subject to the twenty year patent term provisions of 35 U.S.C. 154(a)(2).

[21] Appl. No.: 09/073,350

[22] Filed: May 6, 1998

[51] Int. Cl.$^7$ .................................................. A61B 17/28
[52] U.S. Cl. .......................... 606/208; 606/205; 606/207; 606/174; 81/349; 81/383.5
[58] Field of Search ..................................... 606/205, 207, 606/208, 174; 600/564; 81/345, 349, 383.5

[56] References Cited

U.S. PATENT DOCUMENTS

| | | | |
|---|---|---|---|
| 5,238,002 | 8/1993 | Devlin et al. | 606/205 |
| 5,263,967 | 11/1993 | Lyons et al. | 606/205 |
| 5,618,308 | 4/1997 | Holmes et al. | 606/205 |
| 5,810,865 | 9/1998 | Koscher et al. | 606/205 X |
| 5,810,879 | 9/1998 | De Guillebon | 606/205 |
| 5,904,702 | 5/1999 | Ek et al. | 606/208 |

FOREIGN PATENT DOCUMENTS 0513471   11/1992   European Pat. Off. ............... 606/205

*Primary Examiner*—Michael H. Thaler
*Attorney, Agent, or Firm*—Jones Jain, L.L.P.; Chrittaranjan Nirmel

[57] ABSTRACT

A manually-operable surgical tool, suitable for laparoscopic operations, has separable parts which cooperate to move a pair of end effector elements which can be readily replaced by another pair of end effector elements. A handle portion enables controlled longitudinal movement of an elongate inner element relative to an outer surrounding tubular element. The tubular element has a distal end with a first cleft and a pair of parallel cantilevered inwardly-oriented opposed cam pins. The distal end of the elongate inner element is provided with a second cleft and a transverse force-application pin. The selected end effector elements rotatably fit inside the cleft of the inner element to receive an applied force via the force-application pin. Each end effector element has a blind-ended cutout having an open end for engaging at least with a corresponding one of the cam pins. As the inner element moves longitudinally of the tubular element, the cutouts of the end effector elements rotatably and slidably engage with corresponding cam pins and via the force-application pin have their force-applying portions driven towards each other or moved apart. In another aspect of this invention, pairs of cooperating end effector elements for performing specific surgical operations are stored in modular contamination-resistant containers from which they can be moved to engage directly with the inner and outer elements of the surgical instrument for use. Used end effector elements can be put in a disengagement position by movement of the inner element within the outer tubular element and may be removed.

49 Claims, 15 Drawing Sheets

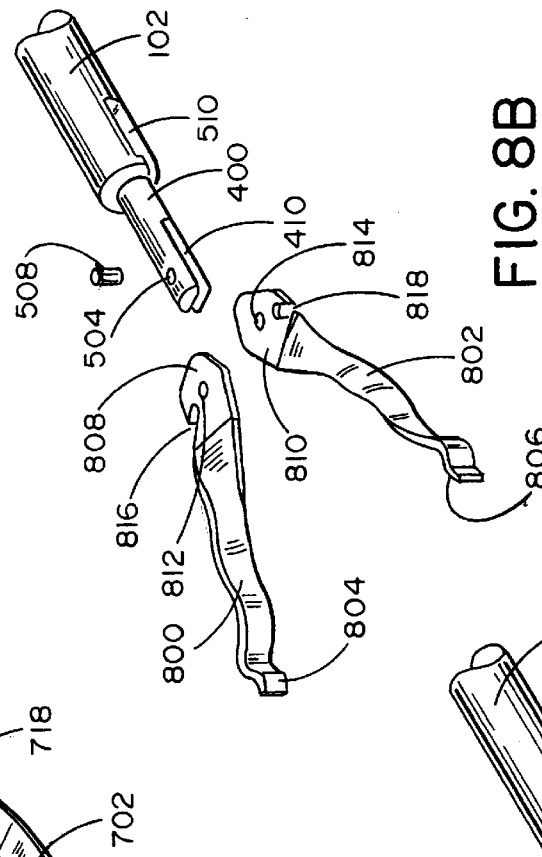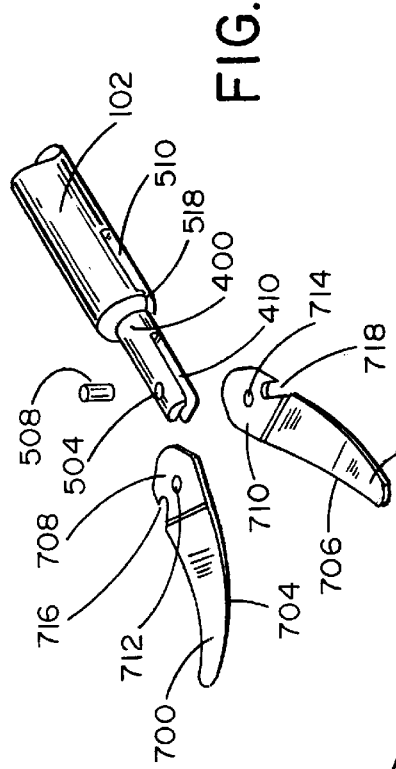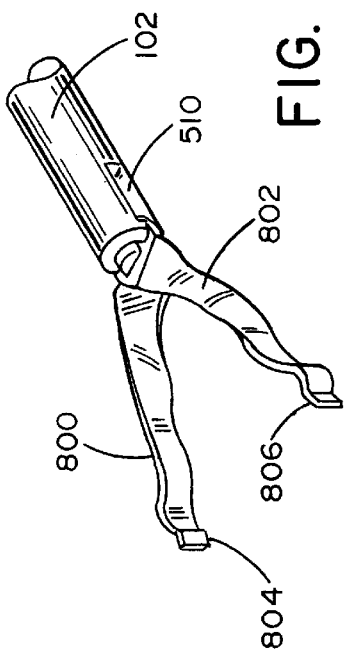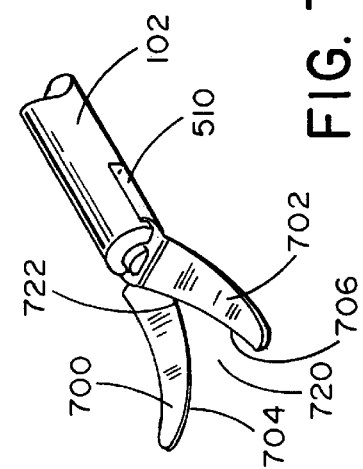

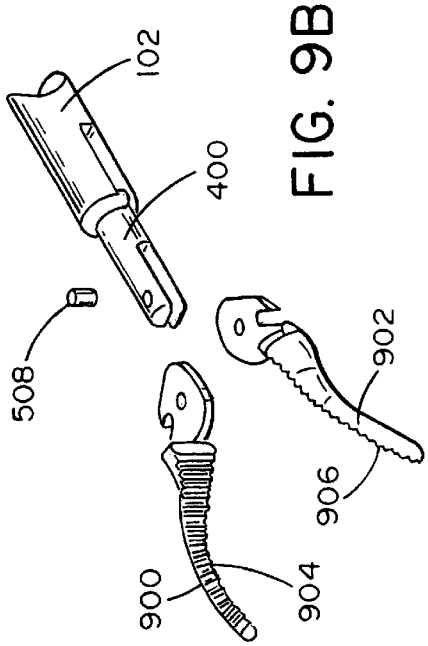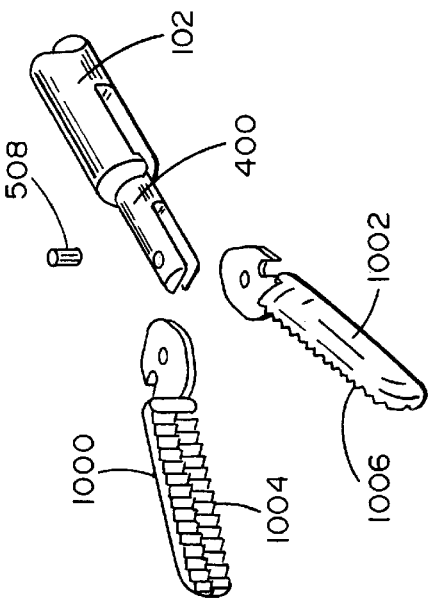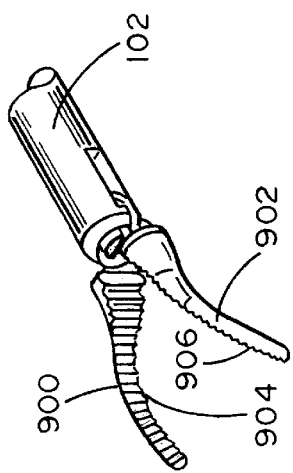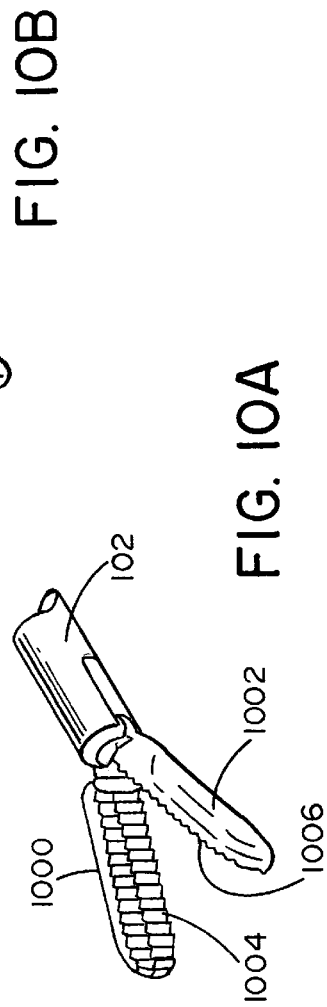

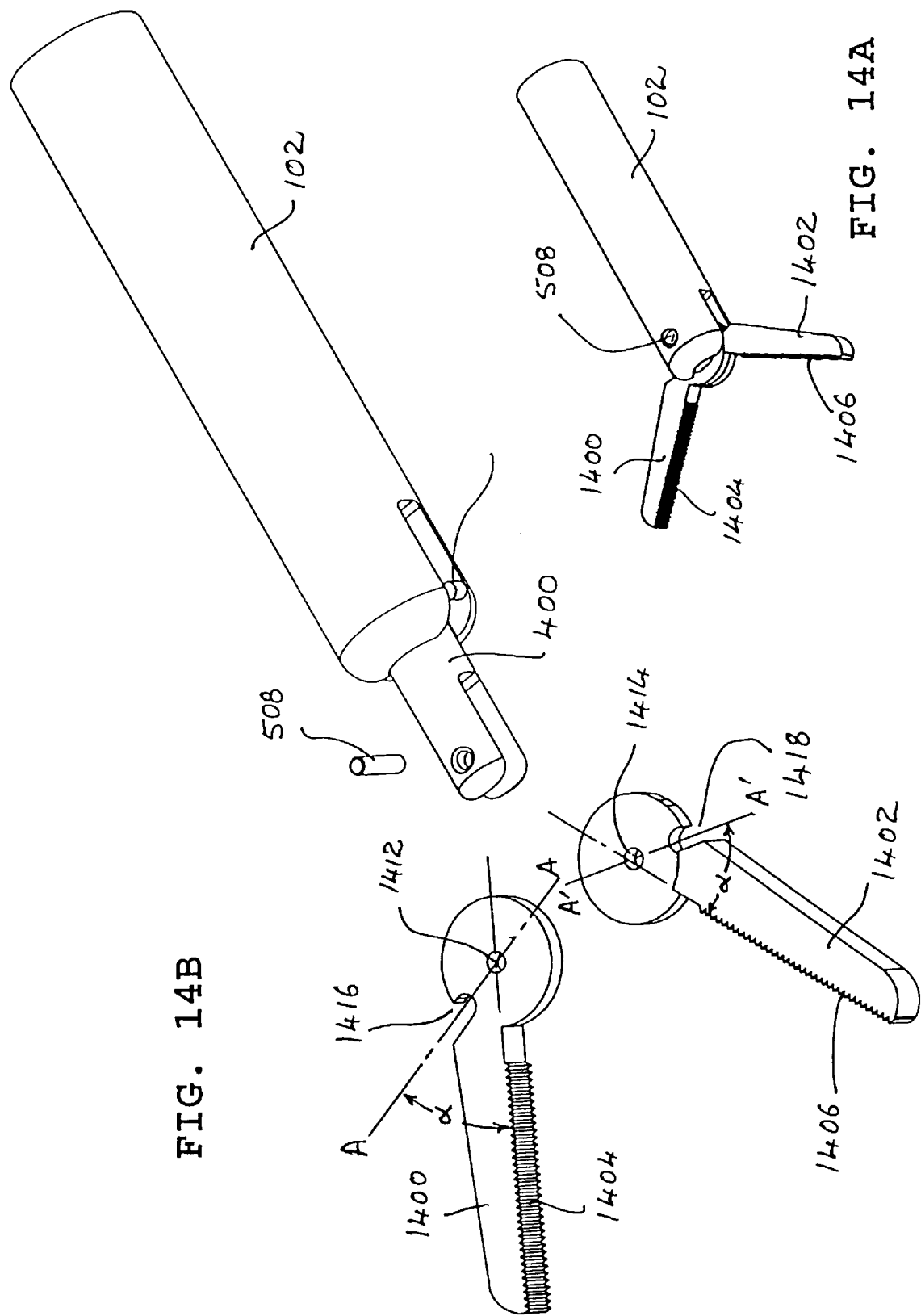

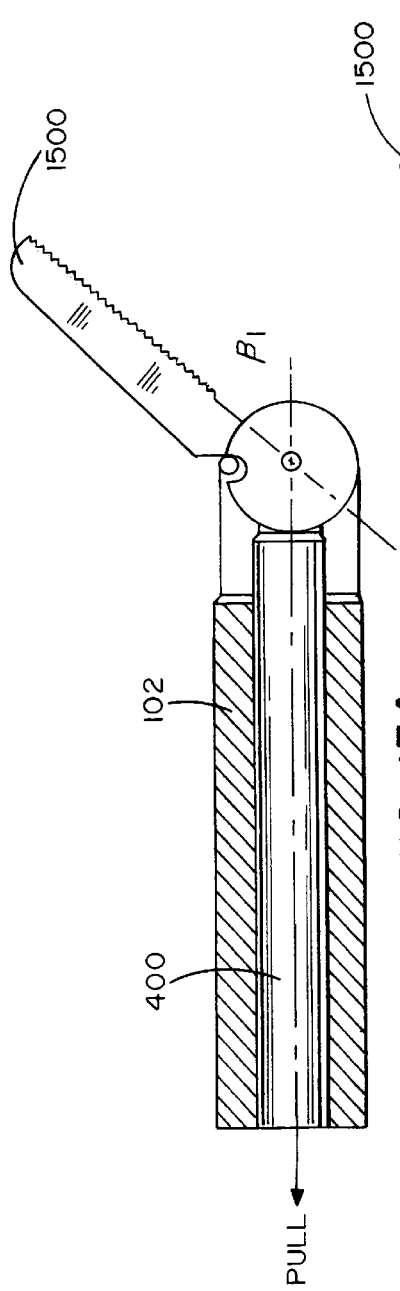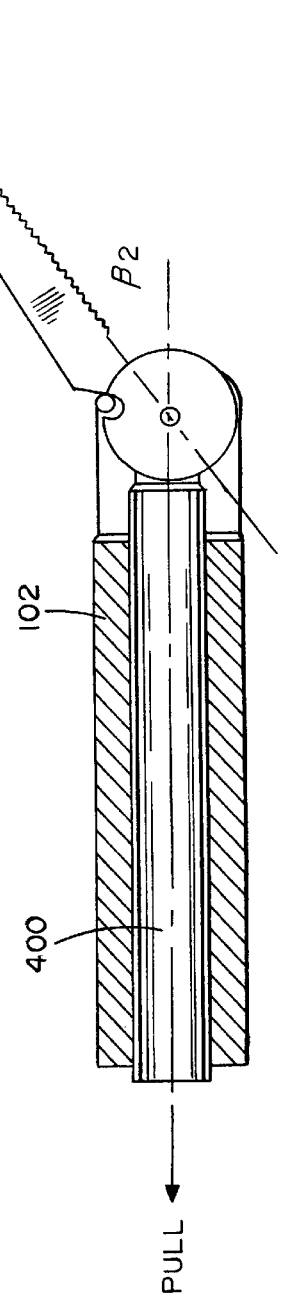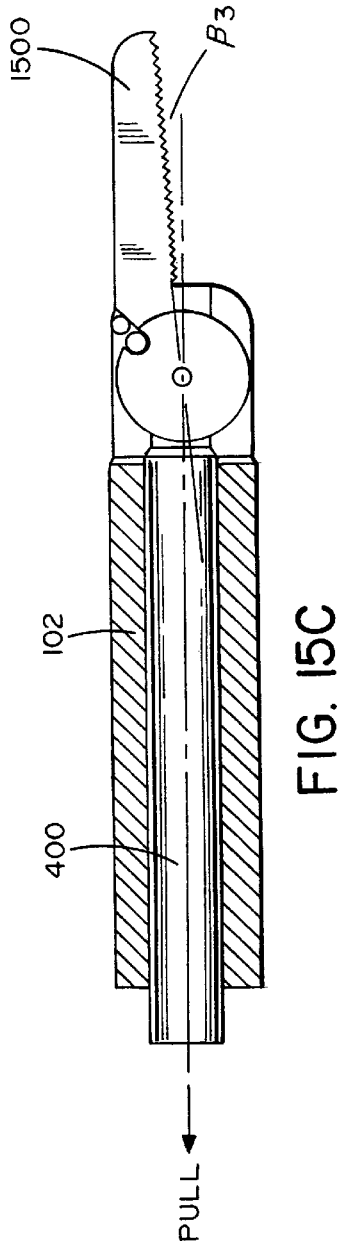

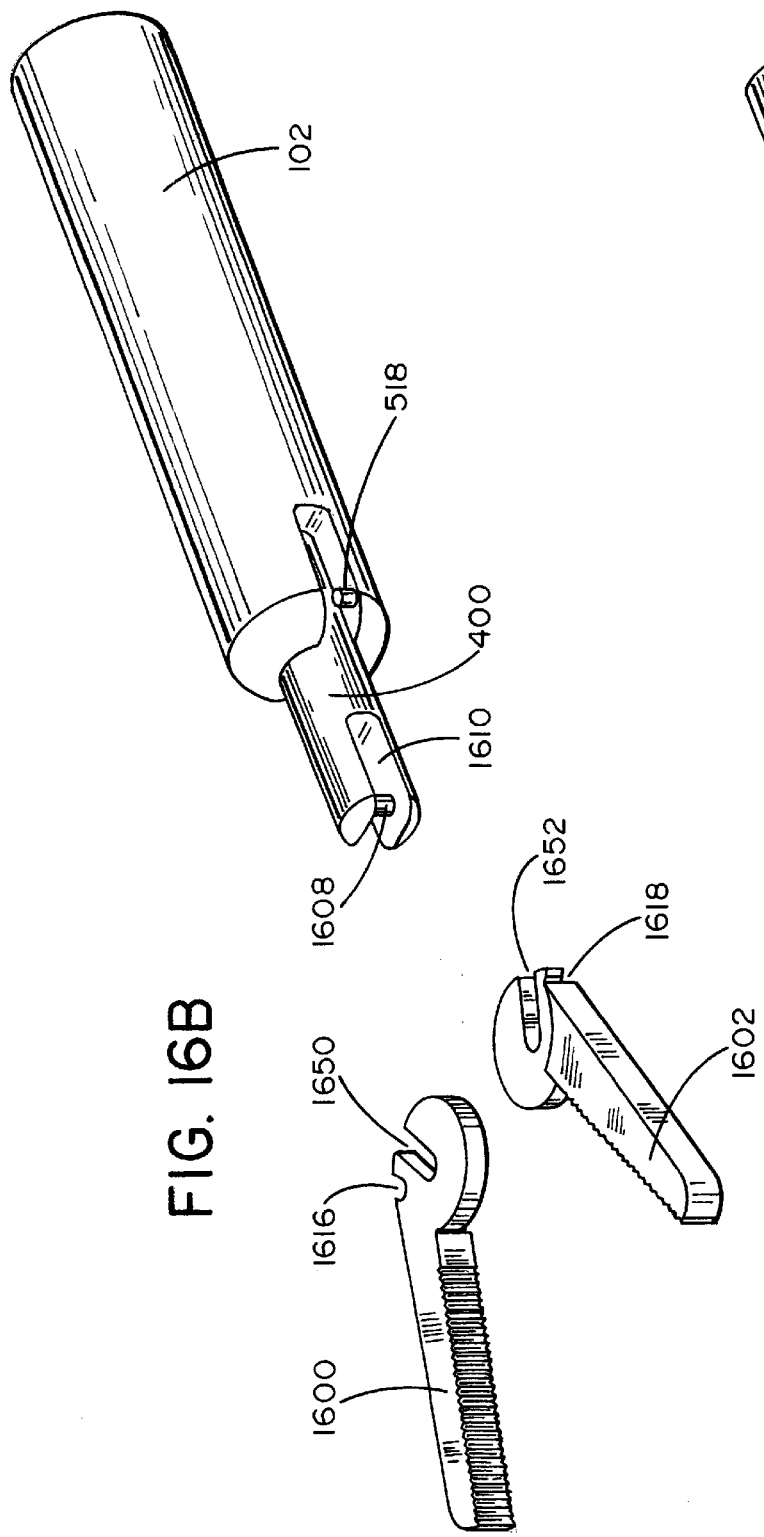
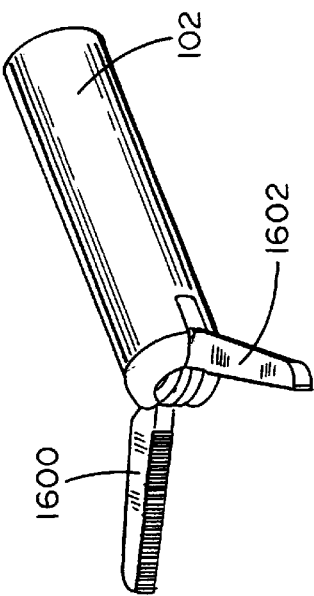

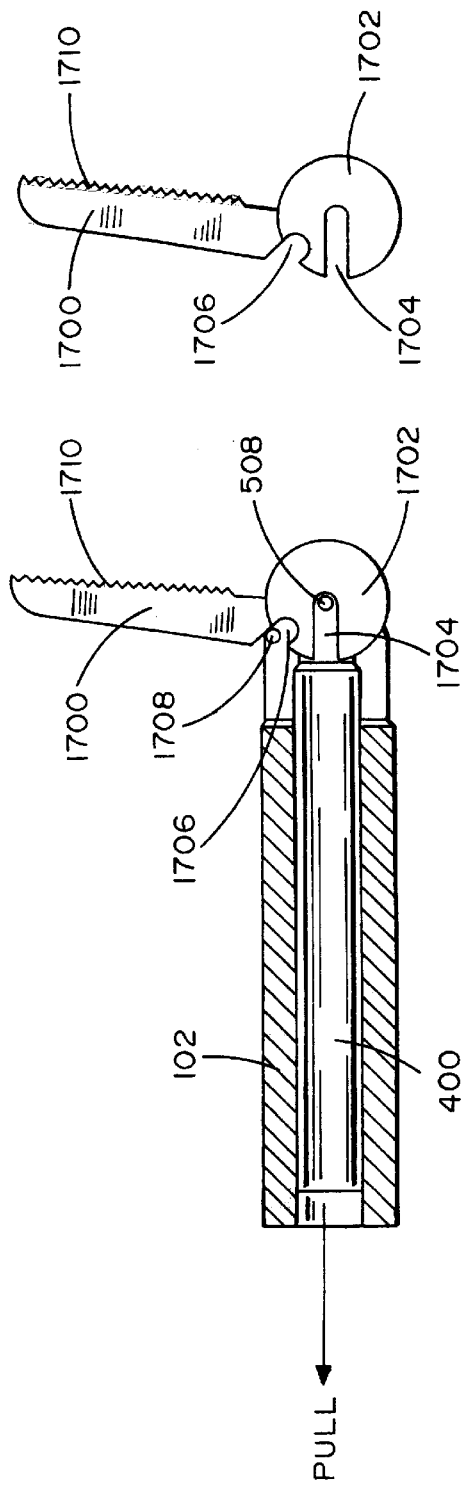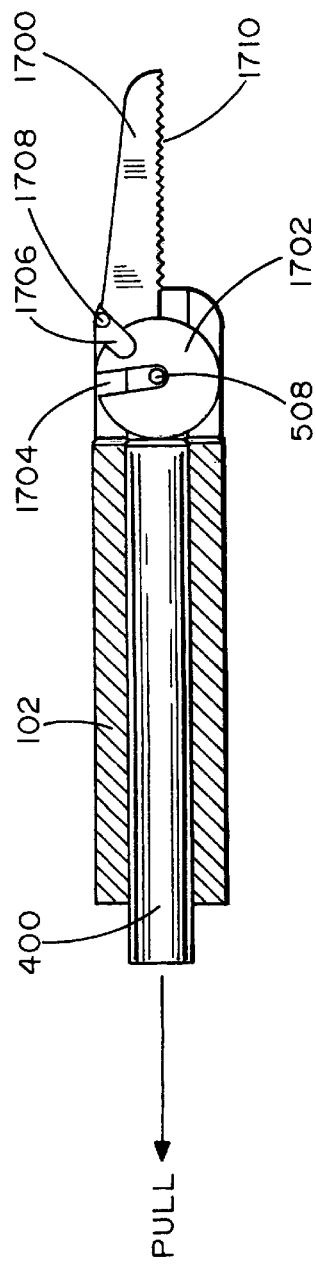
FIG. 17A
FIG. 17B
FIG. 17C

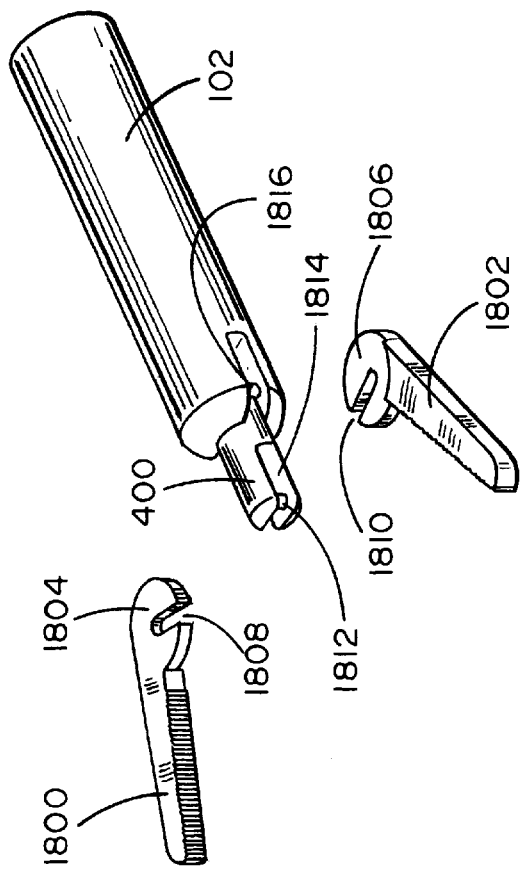
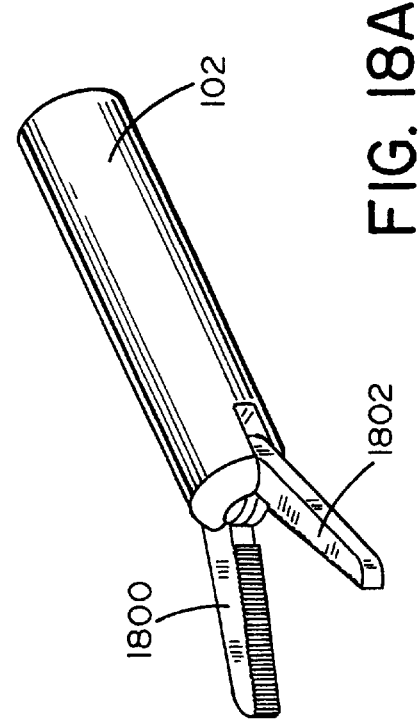
FIG. 18B
FIG. 18A

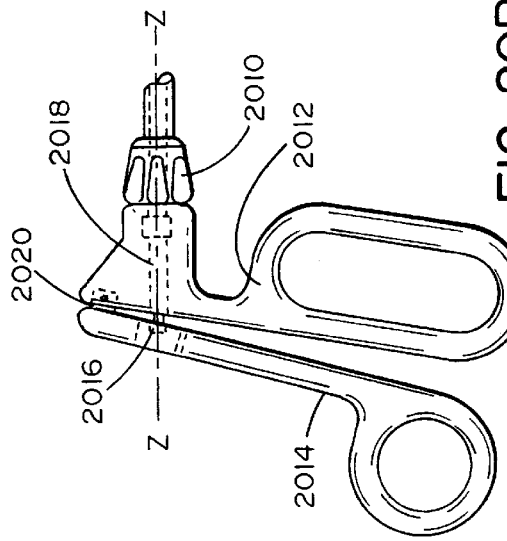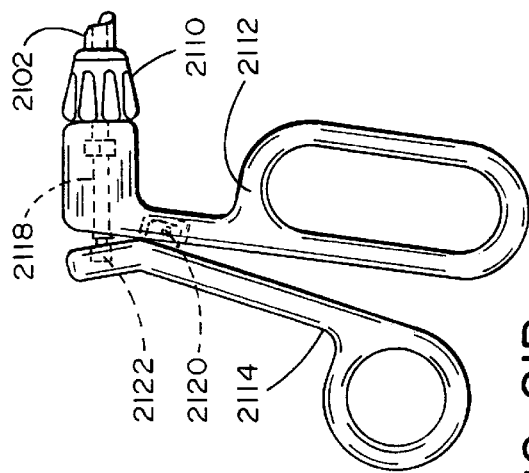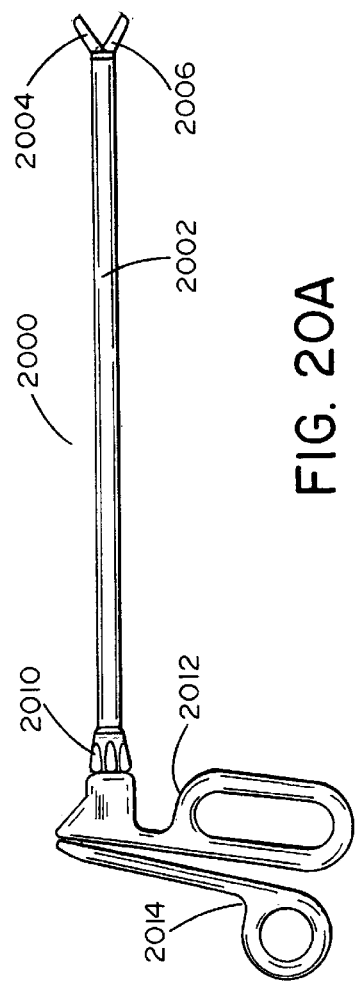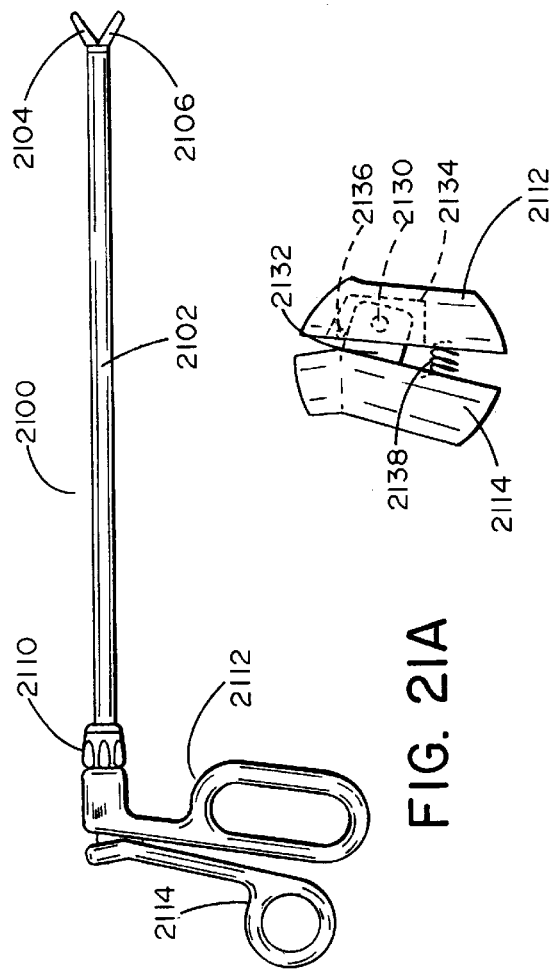
FIG. 20A  FIG. 20B  FIG. 21A  FIG. 21B  FIG. 21C

MANUALLY-OPERABLE SURGICAL TOOL SUITABLE FOR LAPAROSCOPIC OPERATIONS, READILY ADAPTABLE FOR DIFFERENT FUNCTIONS BY QUICK CHANGE OF TISSUE-CONTACTING OPERATIONAL ELEMENTS

FIELD OF THE INVENTION

This invention relates to a manually operable surgical tool to perform a variety of laparosopic surgical functions by application of movable end elements to a patient's tissue. More particularly, it relates to a manually-operable surgical tool having a small-bore elongate portion suitable for laparoscopic surgery involving tissue contact and manipulation, which can be quickly adapted for different functions by easy replacement of modular end effector elements.

BACKGROUND OF THE RELATED ART

There are many circumstances in which surgeons prefer to operate laparoscopically instead of making relatively long incisions which characterize conventional surgery. Typically, a laparoscopic surgical procedure requires a surgeon to form small punctures into a patient's abdominal region, to position via the punctures a plurality of cannulae, and to dispose selected instruments via selected cannulae. Thus, for example, a surgeon may utilize one cannula both for conveying light into the patient's abdominal cavity via optic fibers and for viewing the lighted region via other light-receiving optic fibers and a television monitor. Another cannula may be used to introduce an insufflation gas and/or suction to remove bodily fluids or incidental detritus. Yet other cannulae may be utilized to introduce elongate surgical tools having respective end elements to perform particular functions.

The surgeon must exercise care and dexterity in lighting the zone of interest, carefully holding selected portions of the patient's internal tissues, and performing surgical operations such as incision, cauterization, sawing of bone/tendon, heat-fusion of tissue in lieu of conventional sewing, and the like. Even if the patient is under general anesthesia, the surgeon does not have unlimited time and must operate precisely, carefully, and as quickly as possible. Given the wide variety of surgical techniques and functions, it is therefore highly desirable and cost-effective to have modular tools which permit a variety of operations without requiring a correspondingly large number of separate surgical tools.

There is thus a distinct need for an adaptable surgical instrument in which tissue-contacting/manipulating end elements (often referred to as "end effector elements") may be selected from a modular supply of the same, with the selected elements being quickly and securely fitted operationally to a single hand-held surgical tool body. Furthermore, such an instrument should permit rapid detachment of used modular elements and other operational parts so that they may be quickly exchanged and/or sterilized for subsequent re-use. Various surgical instruments are known for performing at least some of these functions, as exemplified in the patents described below.

U.S. Pat. No. 5,263,967 to Lyons III, et al., titled "Medical Instrument With Dual Action Drive", discloses a medical instrument comprising end effector elements, e.g., jaw members, which are attached by a pivot relative to each other, each effector element being pin-fitted to an irregularly enlarged end of an inner rod slidably contained within a tubular element. The end of the inner element comprises a pair of arms which deliver force required to rotate the cooperating end effectors toward one another. A variety of end effector elements such as grippers, hole-punchers, dissectors, extractors, scissors and clamps, may be employed.

U.S. Pat. No. 5,290,309 to Kothe, titled "Surgical Instrument", discloses an instrument particularly suitable for endoscopy, having closable cooperating jaw parts such as forceps or scissor limbs which are fixed on a pull element. At least one of the jaw parts forms an axis of rotation with the pull element and has a recess in its outer portion. The center point of the recess rotates about a pivot on the pull element. Each recess at least partially surrounds an annular end portion formed in the inside wall of an elongate outer tube, so that each jaw part rotates about this annular portion during closing or opening movement.

U.S. Pat. No. 5,275,615, to Rose, titled "Medical Instrument Having Gripping Jaws", teaches a device having a hand-held portion comprising pivotable handles carried on an instrument body from which projects an elongated tube surrounding a push-pull elongate inner rod. The rod carries a pivotal jaw arrangement and projects outwardly from a distal end of the tube for tissue grasping or gripping. A spherical piston or rack and pinion gear connects the distal end of the rod with the jaw arrangement and a rod travel limit stop is operably connected between the handle, the rod and the instrument body.

U.S. Pat. No. 5,147,357, to Rose, et al, titled "Medical Instrument", discloses a generally similar instrument additionally provided with an electrode carried on the body for supplying energy to the rod and jaw arrangement for cauterization.

Despite the availability of such devices, there still exists a need for a simple hand-operable surgical instrument suitable for laparoscopic surgical procedures which can be readily adapted for a variety of purposes by quick and secure change of end effector elements, with quick replacement of effector elements also to facilitate sterilization of used elements. The present invention is intended to meet this need, and will be best understood by persons of ordinary skill in the art from the following description with appropriate reference to the attached figures.

SUMMARY OF THE INVENTION

It is a principal object of this invention to provide a hand-operable surgical tool suitable for laparoscopic procedures, which employs a very few elements that can be readily taken apart for sterilization and which facilitates quick installment/replacement of tissue-contacting end effector elements.

It is another object of this invention to provide a laparoscopic surgical tool manually operable to employ either a push or a pull force to obtain operational movement of a variety of tissue-contacting and manipulating end effector elements.

It is yet another object of this invention to provide a hand-operable surgical tool particularly suitable for laparoscopic operations, which may be utilized in modular fashion with a variety of end effector elements held in respective sterile containers or "modules" for quick installation on the surgical tool for specific operational uses. It is also an object in another aspect of this invention to provide a method by which a surgeon employing a hand-held operable surgical tool, preferably in a laparoscopic operational procedure, can very quickly install, remove, and/or exchange one or more movable end effector elements.

In a related aspect of the invention, it is a further object to provide a method of mounting end effector elements at an operating end of a hand-operable surgical instrument so that replacement of selected sets of end effector elements can be performed easily.

These and other related objects of this invention are realized by providing in the first aspect of the invention an apparatus which includes an elongate outer tubular element having a proximal end and a distal end formed to have a first cleft, an elongate inner element having a proximal end and a distal end formed to have a second cleft, and a mechanism for controllably moving the inner element longitudinally within the tubular element. A force-application pin is mounted to the inner element to bridge the second cleft and a pair of parallel cantilevered cam pins are mounted on opposite sides of a central axis of the tubular element inside the distal end thereof and oriented transversely across the first cleft.

A pair of cooperating end effector elements, each having a force-receiving portion and a force-applying portion is provided, with each force-receiving portion being formed to pivotably engage with the force-application pin and to simultaneously engage with a respective one of the cam pins, so that relative longitudinal motion between the tubular element and the inner element when in a first direction causes forcible rotations of the end effector elements about the force-application pin to drive the force-applying portions toward each other and when in a second direction causes opposite forcible rotations of the end effector elements about the force-application pin to drive the force-applying portions apart.

Furthermore, in a related aspect of this invention, there is provided a method for quickly mounting a pair of cooperating end effector elements to a hand-held surgical instrument which comprises an elongate outer tubular element having a proximal end and a distal end formed to have a first cleft, an elongate inner element having a proximal end and a distal end formed to have a second cleft, and a mechanism for controllably moving the inner element longitudinally within the tubular element. The method comprises the steps of providing a force-application pin mounted to the inner element so as to bridge the second cleft therein, and providing a pair of parallel cantilevered cam pins, mounted on opposite sides of a central axis of the tubular element inside the distal end thereof and oriented transversely across the first cleft. It includes the further step of providing a pair of cooperating end effector elements each having a force-receiving portion and a force-applying portion, each force-receiving portion being formed to have a single blind cutout formed to receive therein both the force-application pin and a corresponding cam pin. Each force-receiving portion is also formed to pivotally engage with the force-application pin and to simultaneously engage with a respective cam pin, whereby relative longitudinal motion between the tubular element and the inner element when in a first direction causes forcible rotations of the end effector elements about the force-application pin to drive the force-applying portions toward each other and when in a second direction causes opposite forcible rotations of the end effector elements about the force-application pin to drive the force-applying portions apart.

BRIEF DESCRIPTION OF THE DRAWING

FIG. 7A is a perspective view of a scissors-type set of end effector elements installed in the proximal end in a surgical instrument according to a first preferred embodiment; and FIG. 7B is an exploded view of the same.

FIG. 8A is a perspective view of another preferred embodiment of this invention provided with a pair of end effector gripping elements; and FIG. 8B is an exploded view of the same.

FIG. 9A is a perspective view of another preferred embodiment of this invention provided with a pair of curved serrated clamp elements; and FIG. 9B is an exploded view of the same.

FIG. 10A is a perspective view of another preferred embodiment of this invention provided with a pair of relatively wide, straight, serrated clamp elements; and FIG. 10B is an exploded view of the same.

FIG. 14A is a perspective view of an embodiment in which cooperating clamp elements, generally like those in the embodiment of FIG. 11A, are installed in a pull-operation arrangement; and FIG. 14B is an exploded view of the same.

FIGS. 15A, 15B and 15C are partially-sectioned views of an elongate clamp arrangement per FIGS. 14A and 14B to illustrate the pull-operation of an exemplary end effector element thereof at different stages from a wide-open, through a partially closed, to a fully closed position.

FIG. 16A is a perspective view, and FIG. 16B is an exploded view, of an elongate clamp arrangement in which each of the cooperating end effector elements is provided with two outside radial grooves in a push-operation arrangement.

FIG. 17A is a side view of an elongate clamp end effector element provided per FIGS. 16A and 16B with a first groove for engaging with a pin of a pull rod and a second groove for engaging with a cantilever pin in an outer tubular element; and FIGS. 17B and 17C, respectively, are partially-sectioned views to illustrate push-operation from an installment position to a full-closed position.

FIG. 18A is a perspective view, and FIG. 18B is an exploded view, of an elongate clamp arrangement in which each of the cooperating end effector elements is provided with a single groove oriented radially inward which simultaneously engages with a drive pin provided on a central elongate push rod and a cantilevered pin provided on an outer tubular element, in a push-operation arrangement.

FIG. 20A is a side view of a push-operation embodiment of this invention, and FIG. 20B is an enlarged view of the hand-gripped handle portion thereof.

FIG. 21A is a side view of a pull-operation embodiment of this invention; FIG. 21B is an enlarged view of the hand-gripped handle portion thereof; and FIG. 21C is a further enlarged view of a portion at which the two cooperating halves of the handle pivotably engage with each other.

DETAILED DESCRIPTION OF THE PREFERRED EMBODIMENTS

Figure 1:
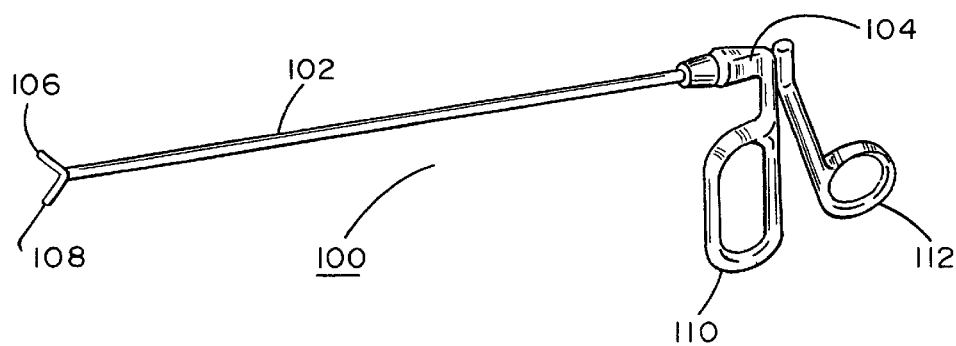
FIG. 1 is a perspective side view of an exemplary hand-operable surgical tool of a type generally employed in laparoscopic or endoscopic surgical procedures.
Figure 2:
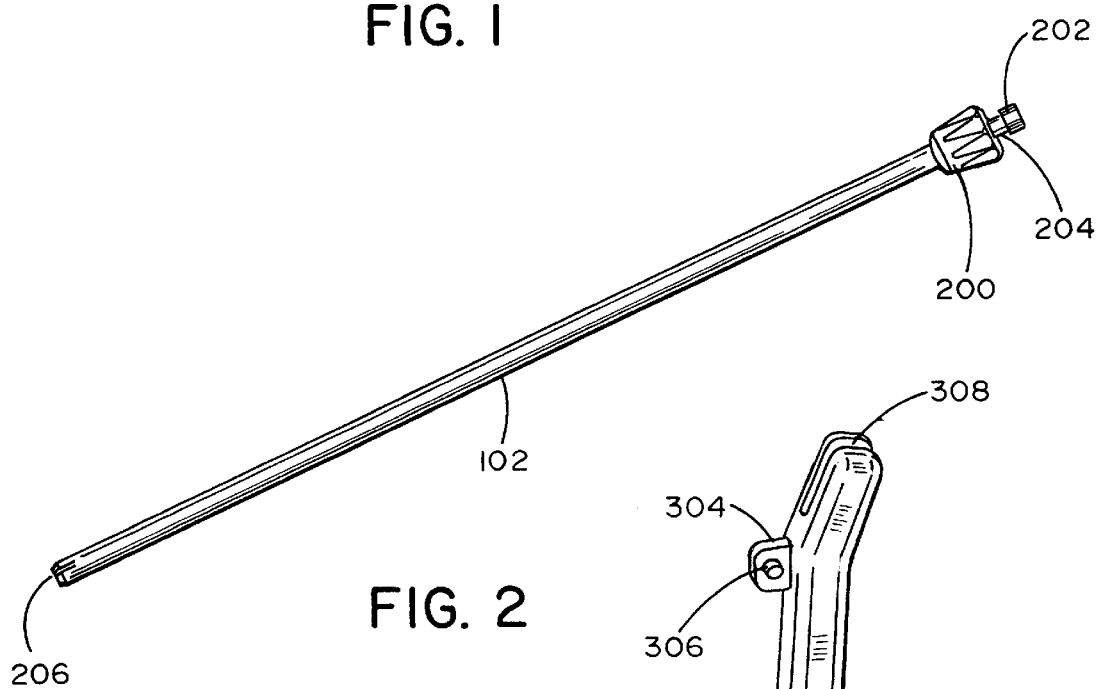
FIG. 2 is a side view of a tubular element in the surgical tool per FIG. 1.

As best seen in FIG. 1 the hand-held surgical instrument 100 according to a preferred embodiment of this invention has an elongate body portion defined by a tubular element 102 mounted at a proximal end to a two-part handle mechanism 104.

At the distal end of the elongate body of the instrument 100 is typically provided a pair of cooperating end effector elements 106, 108 which rotate relative to each other about a common axis when a user moves handle elements 110 and 112 relative to each other. Handle element 110 preferably has a closed loop sized and shaped to comfortably accommodate one or more fingers of the user, while cooperating handle element 112 preferably has a somewhat smaller closed loop shaped and sized to comfortably accommodate the user's thumb.

The surgeon will initially manipulate handle elements 110, 112 so that the end effector elements 106, 108 are rotated close to each other and are generally aligned with the longitudinal axis of tubular element 102. The distal end of the surgical instrument is then introduced from the outside of the cannula (not shown) and along its length at least until the end effector elements 106, 108 exit the inner end of the cannula into the patient's abdominal cavity. The surgeon may then manipulate the instrument and the cannula as appropriate to access the surgical site. Further manipulation of hand elements 110, 112 and corresponding operation of end effector elements 106, 108 may be utilized for assorted surgical functions, e.g., grasping and/or cutting tissue, compressing a blood vessel, or the like.

Depending on the patient's condition and the surgical procedure to be practiced, a surgeon may find it helpful or perhaps even necessary to employ different end effector elements introduced serially via a particular cannula to perform a series of surgical operations. If the surgeon were to employ an entirely different tool with each particular set of end effector elements a relatively large number of surgical instruments would be required. It is therefore highly desirable to have the facility to quickly and in a non-contaminating manner replace a given pair of cooperating end effector elements by another selected pair of end effector elements, and to continue using a particular surgical instrument body.

Tubular element 102 preferably is a length of tubing of small cross-section. It may be made of a sterilizable metal such as stainless steel, or even of a relatively stiff, smooth-walled plastics material if the instrument is intended to be discardable. Tubular element 102 may be provided with a proximal head 200 having local irregularities to facilitate easy grasping by a user whose gloved hands may be wet or slippery through contact with bodily fluids. At the proximal end of tubular element 102 is provided a small length 204 having an outer diameter somewhat smaller than that of head 200 and an enlarged portion 202 for engagement into handle portion 110 in known manner.

The distal end of tubular element 102 is also formed to have a parallel-sided longitudinally-oriented inward cleft 206 with certain internal structural features described below.

Figure 3:
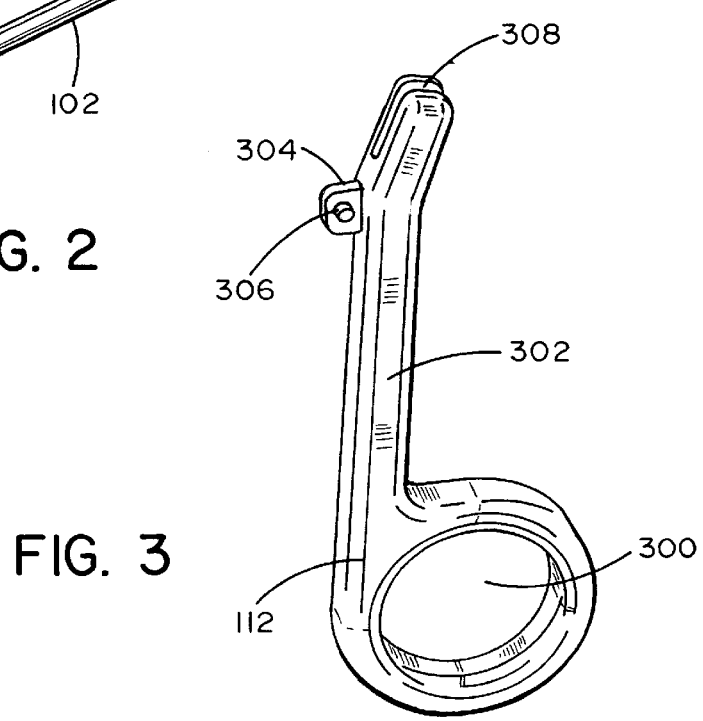
FIG. 3 is a perspective view of a pivotable portion of the hand-held handle end of the surgical tool per FIG. 1.

As best seen in FIG. 3, handle element 112 has a thumb-accommodating loop 300 connected to an arm 302 which at an upper forward portion has a bracket 304 and a transverse pin 306. Handle element 112 pivotably engages handle element 110 via pin 306 in one embodiment of the handle mechanism. At the upper or distal end of arm 302 is provided a socket 308 shaped and sized to closely but movably receive therein a proximal end portion of an elongate rod-like element 400 which is to be positioned to slide controllably along and inside the length of tubular element 102.

Figure 4:
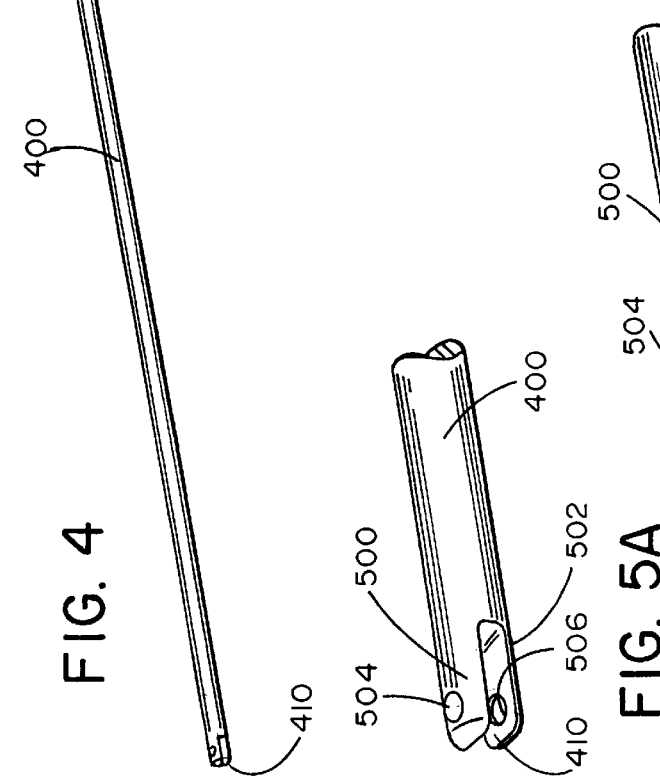
FIG. 4 is a side view of an exemplary elongate rod-like element slidably movable within a tubular element per FIG. 2 in the surgical instrument per FIG. 1.
Figure 6:
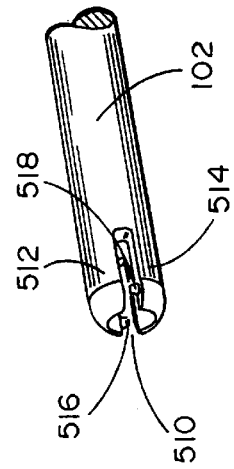
FIG. 6 is an enlarged view of the proximal end of the rod-like element per FIG. 4.

FIG. 4 is a side view of this elongate rod-like inner element 400 which has a length preferably a little longer than that of the outer tubular element 102 within which it is slidably positioned during use. The proximal end of inner element 400, as seen in greater detail in enlarged view in FIG. 6, has a reduced diameter portion 402 and an extreme proximal end 404 an outer surface of which comprises curved annular portions 406 and 408. As will be appreciated from joint reference to FIGS. 1, 3, 4 and 6, in the surgical instrument 100 the proximal end portion 404 of inner element 400 fits into socket 308 of handle element 112 which pivots relative to handle 110 under the user's control. The shape and size of socket 308 and extreme proximal end 404 of inner element 400 are selected to permit relative movement therebetween while they are engaged closely and the instrument should feel, for example, like a good pair of scissors which can be easily operated but the components of which are not sloppily connected to each other.

Figure 5A:
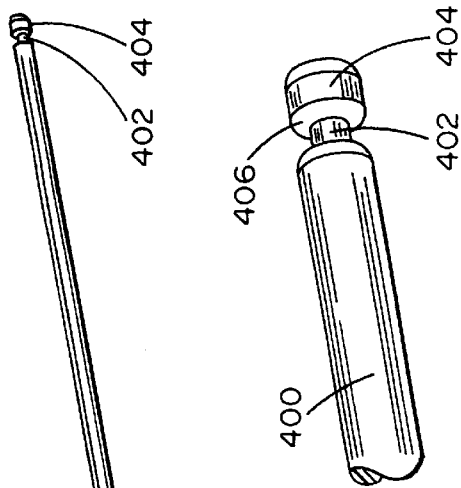
FIGS. 5A and 5B are respective enlarged views of different geometries for the distal end of the rod-like element per FIG. 4.
Figure 5B:
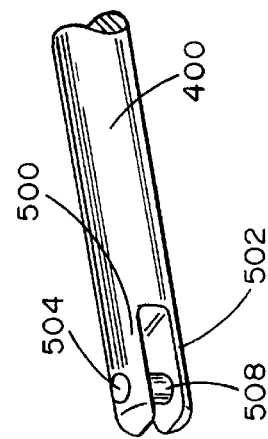

The extreme distal end of inner element 400 is also provided with its own longitudinal, parallel-sided inner cleft 410. One variation of this structure is shown in somewhat enlarged view in FIG. 5A. In this variation, cleft 410 results in the provision of two relatively narrow parallel distal arms 500, 502 through both of which are drilled respective coaxial through-apertures 504 and 506. A pin 508 may then be force-fitted or otherwise securely located in known manner through-apertures 504 and 506. Pin 508 would pass through a pair of cooperating end effector elements (in a manner to be described in detail) but the end effector elements are omitted from FIG. 5B for simplicity.

Figure 5C:
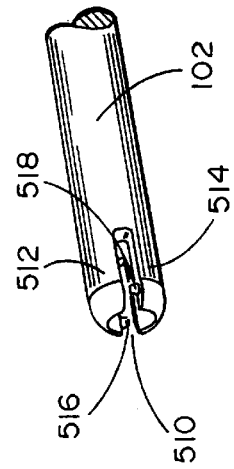
FIG. 5C is an enlarged view of the distal end of the tubular element per FIG. 2.

As best seen in FIG. 5C, the distal end of tubular element 102 is provide a longitudinal cleft 510 which is then bracketed by a pair of opposed longitudinal arms 512, 514. Extended inwardly from planar surfaces of arms 512 and 514, on opposite sides of cleft 510, are provided two parallel cantilevered pins 516, 518 which extend across just less than half the width of cleft 510. The reason for this will become apparent from the following description.

Incision of soft tissue can be effected by a single sharp edge, e.g., with a scalpel, or in the alternative by shearing of tissue between a pair of sharp-edged elements forcibly driven towards each other as in a pair of scissors. FIG. 7A illustrates such a pair of end effector scissors elements 700, 702 operatively fitted within cleft 410 of inner element 400 and cleft 510 of tubular element 102. FIG. 7B is an exploded view of such an assembly.

In this embodiment, end effector scissor elements 700, 702 have respective force-applying portions provided with respective sharp edges 704 and 706. End effector scissors elements 700, 702 also have respective force-receiving portions 708, 710 provided with respective through-apertures 712, 714 sized to rotatably receive therethrough the force-applying pin 508 mounted transversely of cleft 410 in inner element 400. End effector scissors elements 700, 702 are provided with respective cutouts (or slots) 716, 718 which have respective open ends on opposite sides of the corresponding sharp edges 704, 706. Cutouts 716, 718 are sized to rotatably and slidably fit to corresponding cam pins 516, 518 mounted transversely of cleft 510 in the distal end of tubular element 102.

The embodiment illustrated in FIGS. 7A and 7B, at an intermediate stage in its assembly, would require that force-receiving portions 708, 710 be received within cleft 410 with through-apertures 712 and 714 aligned coaxially with through-apertures 504, 506 of inner element 400 so that force-applying pin 508 may be forcibly driven into place to securely and rotatably retain end effector scissors elements 700, 702 to inner element 410. End effector scissors elements 700 and 702 are then respectively rotated so that they individually both slidingly and rotatingly engage with corresponding cam pins 516, 518 as inner element is drawn further into tubular element 102. Upon connection of the proximal end of inner element 400 to handle element 112, by appropriate manipulation of the handle mechanism the user may controllably exert a pulling force on the proximal end of inner element 400. This force would then be transmitted via pin 508 to end effector scissors elements 700 and 702. However, because their respective cutouts or slots 716, 718 would then essentially cam over corresponding cam pins 516, 518, the corresponding sharp edges 704 and 706 would be pressed towards each other as end effector scissors elements 700, 702 rotate to close the gap 720 therebetween.

The shearing action of the embodiment per FIGS. 7A and 7B involves some translation by them longitudinally along the axis of tubular element 102 and simultaneous rotation about pin 508 to generate scissors-type shearing action on tissue present between sharp edges 704 and 706. This is distinguishable over the shearing provided by the two elements of conventional scissors elements which directly pivot to each other and in which the cutting or shearing point only moves forwardly of the pivot as cutting is effected. There is, however, an unusual advantage provided by the present invention as just described. In the embodiment per FIGS. 7A, 7B, in which a pulling force applied to the inner element 400 causes it, pin 508, and end effector scissors elements 700 and 702 to move backward towards the proximal end of tubular element 102 while the scissors shearing action takes place, the cutting point 722 which otherwise would normally travel forwardly of the sharp edges in conventional scissors does so by a smaller distance. Once a surgeon develops proficiency with the instrument he or she should be able to make precise incisions with better control than with conventional scissors-type instruments in which the cutting point actually moves forward.

FIGS. 8A and 8B illustrate another variation, in which are provided a pair of cooperating end effector grasping elements 800, 802. Since the only distinction between this embodiment and the one illustrated in FIGS. 7A and 7B lies in the form and function of the respective pairs of end effector elements, a detailed description of the other connected elements is omitted.

Note that force-applying portions of end effector grasping elements 800, 802 are illustrated as having arbitrary shapes. This is intended to convey to the reader that any suitable shapes may be chosen, e.g., to permit a surgeon to reach around a portion of the patient's anatomy such as an intestine or a blood vessel, to operate the end effector grasping elements so that their distal or tip portions 804, 806 may be driven toward each other to grasp only tissue lying therebetween. In other words, the surgeon can avoid applying force to intermediate tissue except as the facing surfaces of the tip portions 804 and 806 cooperatively squeeze on tissue located only thereat. The force-receiving portions 808, 810 of these embodiments may be essentially the same as corresponding force-receiving portions 708, 710 of the previously described embodiment. Other similarities include through-apertures 812, 814 and respective cutouts 816, 818. The operation of the end effector grasping elements 800, 802 is otherwise generally similar to the corresponding operation of end effector scissors elements 700, 702 and, therefore, will not be described in greater detail.

The versatility of the invention can be understood better by reference to FIGS. 9A and 9B which show an embodiment including a pair of generally curved-profile end effector elements 900, 902 provided with matching non-slip, e.g., serrated, tissue-contacting surface portions 904, 906. Note that end effector curve grasping elements 900, 902 are relatively slim or narrow and, particularly because of their non-slip tissue-contacting surface portions, may be used to delicately hold small portions of tissue in confined surgical sites. The assembly and operation of this embodiment is otherwise similar to that of the embodiments per FIGS. 7A, 7B and 8A, 8B. They will therefore not be described further in detail.

It should be noted, however, that the particular advantage discussed with respect to end effector scissors elements 700, 702, i.e., that the cutting point need not move significantly forward as the surgeon operates the surgical tool, will not be realized in a same way in the embodiment illustrated in FIGS. 9A and 9B.

Any minor adjustments which the surgeon must make to adjust to the particular operational aspects of any of the embodiments described above should be very easy to learn. The end effector elements are generally quite small, and the fact that their force-receiving portions experience both translation and rotation should pose no problem once the surgeon develops familiarity with the surgical instrument.

FIGS. 10A and 10B illustrate details of another variation, namely, one in which a pair of end effector grasping elements 1000, 1002 have relatively wide force-applying portions 1004, 1006 provided with corresponding matchingly-shaped non-slip surfaces including respective serrations. Such a pair of end effector grasping elements may be utilized to advantage to grasp small/slim bones or tendons which may otherwise tend to slip when grasped. In other respects the structure, assembly, and operation of this embodiment are comparable to those of the previous described embodiment.

The embodiments described hitherto all have the blind cutouts formed in the corresponding end effector elements so that each cutout has its open end away from the force-applying edge or surface of the corresponding end effector element. The blind end of each cutout is located radially inward and adjacent to the through-aperture for receiving force-applying pin 508 in each case. Each blind cutout engages slidingly and rotatingly with a corresponding cam pin provided in tubular element 102, such that retraction of the distal end of inner element 400 into the distal end of outer tubular element 102 causes the end effector elements to rotate towards each other to cut or grasp tissue positioned therebetween. Such an arrangement may generally be referred to as a "pulling configuration" and is one in which the handle elements are operated by the user to apply a pulling force on the proximal end of the inner element 400 to cause the end effector elements to move towards each other.

Some surgeons may prefer an alternative mode of operation in which it is necessary for the handle mechanism to be operated so that a pushing force, optionally against a small biasing force provided by a spring (not shown) between handle elements 110 and 112, is applied to the proximal end of the inner element 400 so that its distal end is pushed in a direction longitudinally and outwardly of the distal end of outer element 102 in order to cause rotation of end effector elements towards each other. Such a structure requires that the blind cutouts be provided on the same side as the force-applying sharp edges or tissue-contacting surface portions of the respective end effector elements. This is best understood with reference to FIGS. 11A and 11AB. Such an arrangement may be referred to as a "pushing configuration".

Figure 11B:
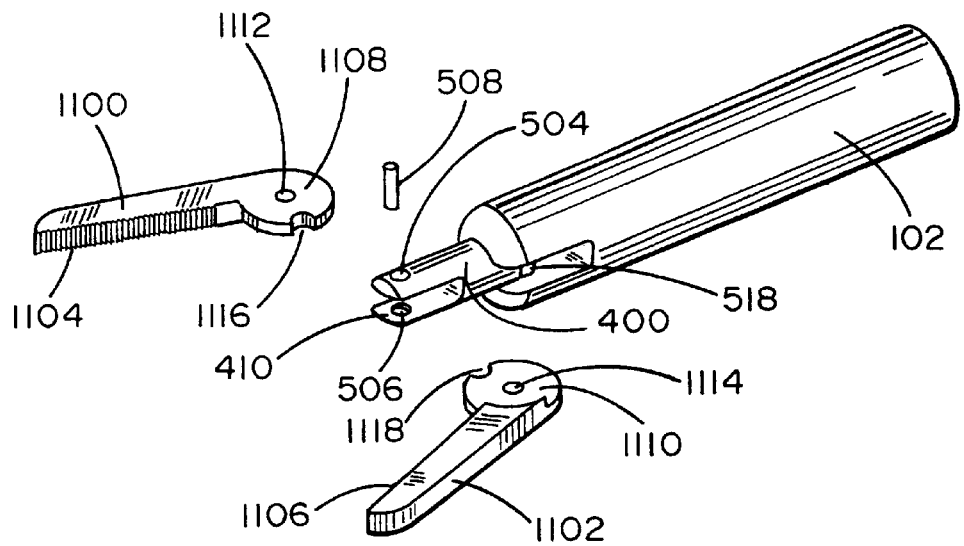
FIG. 11B is an exploded view of the same.
Figure 11A:
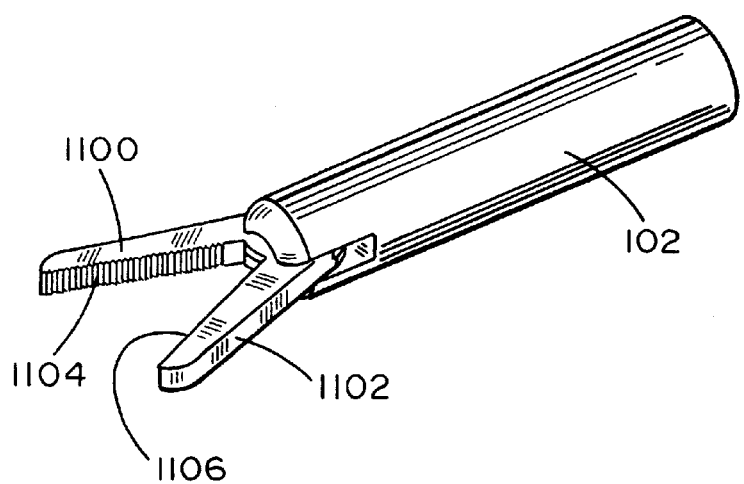
FIG. 11A is a perspective view of another preferred embodiment of this invention provided with a pair of straight, elongate, relatively narrow, serrated clamp elements.

FIG. 11A shows a pair of end effector grasping elements 1100, 1102 having long narrow force-applying surface 1104, 1106 which may be provided respective non-slip characteristic, e.g., by serration or otherwise in known manner. FIG. 11B shows that the end effector elements 1100 and 1102 have respective blind cutouts 1116, 1118 with their respective openings on the same side as the corresponding tissue-contacting surfaces 1104, 1106 respectively. With such an arrangement, the force-receiving portions 1108, 1110 of end effector grasping elements 1100, 1102 are received within cleft 410 of inner element 400, and pin 508 is forcibly fitted into through-apertures 504, 506 and simultaneously into through-apertures 1112 and 1114. The end effector elements 1100, 1102 must be rotated away from each other until their respective blind cutouts 1116, 1118 engage with respective cam pins 516, 518 of outer tubular element 102.

With the pushing configuration as described in the immediately preceding paragraph, the pushing force applied by the handle mechanism to the proximal end of inner element 400 will cause the applied force at pin 508, and the camming engagement of cutouts 1116 and 1118 slidingly and rotatingly with respective cam pins 516 and 518, to rotate end effector grasping elements 1100, 1102 toward each other to forcibly grasp any tissue located between their force-applying surfaces 1104, 1106. To the contrary, when the user (or a biasing spring if one is included) causes handle elements 110, 112 to move so as to apply a pulling force on the proximal end of inner element 400, the end effector grasping elements 1100, 1102 will rotate away from each other.

Figure 12A:
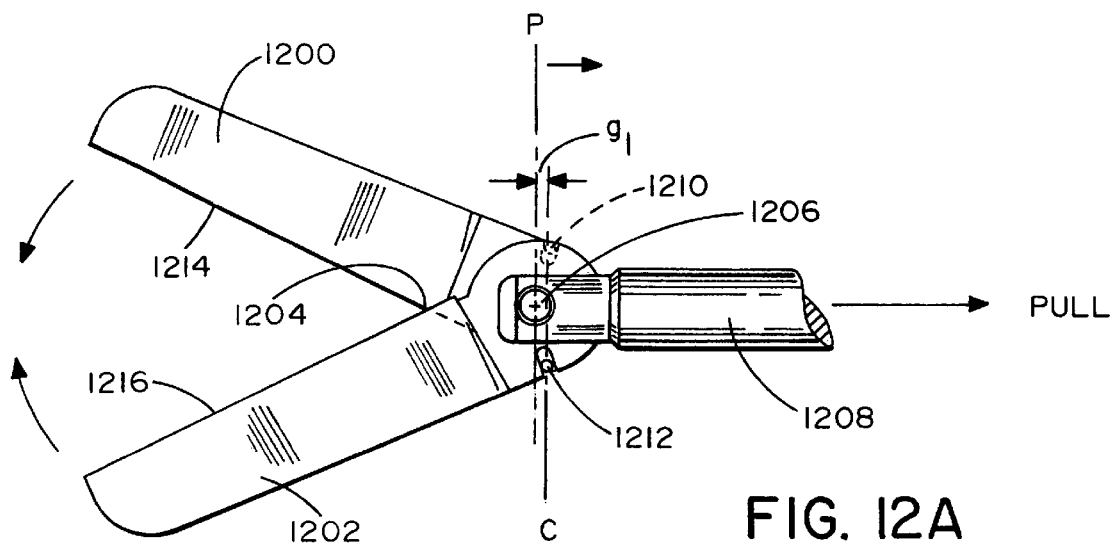
FIGS. 12A, 12B, and 12C are side views of a scissors-type set of end effector elements in wide-open, partially-closed, and completely-closed positions, respectively, in a pull-operation arrangement.

FIG. 12A is a side view of a portion of the distal end of a pull configuration instrument employing a pair of end effector scissors elements 1200, 1202 at their widest-apart disposition, one in which tissue-intersection point 1204 is closest to pin 1206 fitted into the cleft end of inner rod 1208. During operation of such an arrangement, user will apply a pulling force by means of the handle mechanism 104 in the direction indicated by the arrow marked "PULL". Although the tubular portion of the outer element 102 is omitted for simplicity, cam pins 1210, 1212 which would be mounted therein in the complete instrument are shown for purposes of this explanation.

Figure 12B:
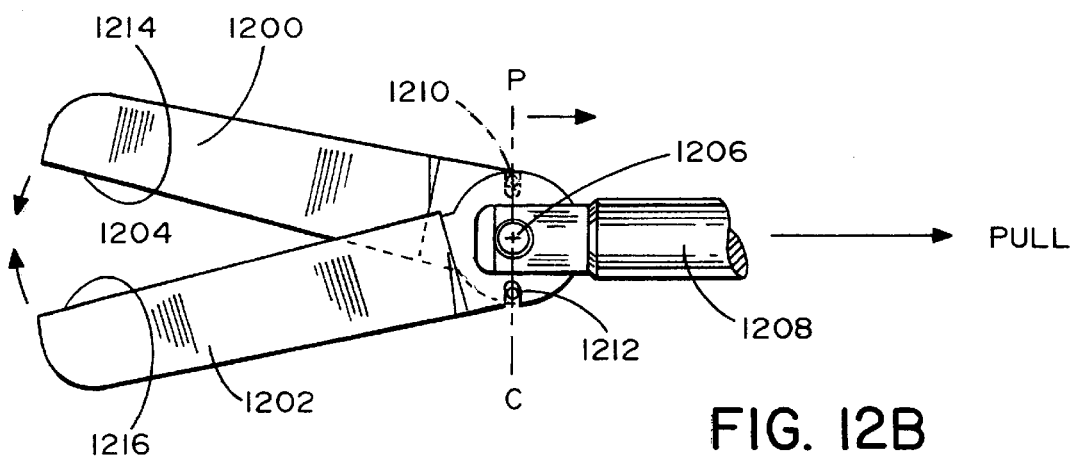
Figure 12C:
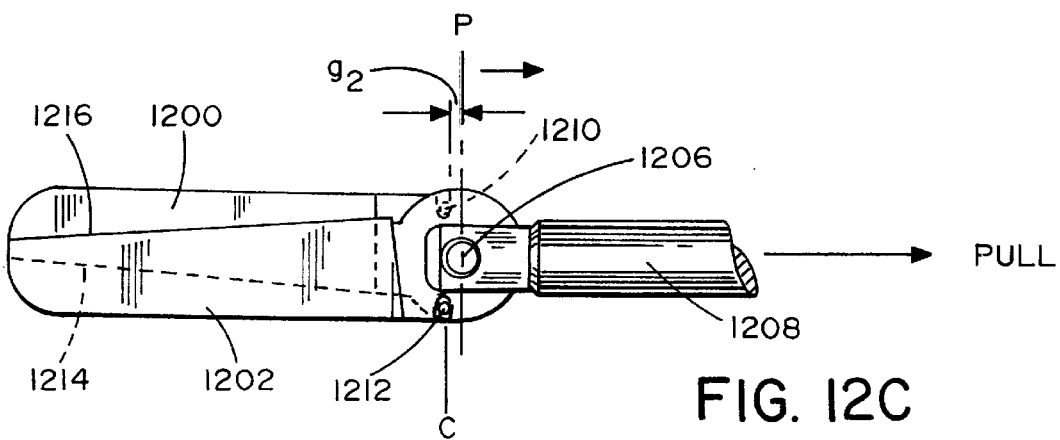

For present purposes, the transverse axis "C" passing through both cam pins 1210, 1212, perpendicular to the longitudinal direction of both the inner element 1208 and the associated tubular element (not shown), may be regarded as stationary. Movement of inner element 1208 will result in a transverse axis "P" passing through the center of pin 1206 to move in translation. In the disposition shown in FIG. 12A, pin 1206 is forward, i.e., to the left, of axis "C" by a distance "$g_1$". As the user applies a pulling force on inner element 1208, pin 1206 will move until, in the disposition illustrated in FIG. 12B, it is coaxial with axis "C" of cam pins 1210, 1212. Note that although both end effector elements 1200, 1202 have moved translationally toward the handle element along with pin 1206, the tissue-intersection point 1204 where the sharp edges 1214, 1216 of the end effector scissors elements 1200, 1202 meet to cut tissue has advanced forward by a larger amount.

Finally, upon sufficient motion of inner element 1208 under the pulling force "P" applied by the user, the center of pin 1206 will be located rearwardly of cam pins 1210, 1212 by a distance "$g_2$", and the cutting edges of the end effector scissors elements will have contacted each other over their entire lengths. It is in this disposition that the distal end of the surgical instrument will be introduced through the cannula into the patient's body to access the surgical site.

Figure 13A:
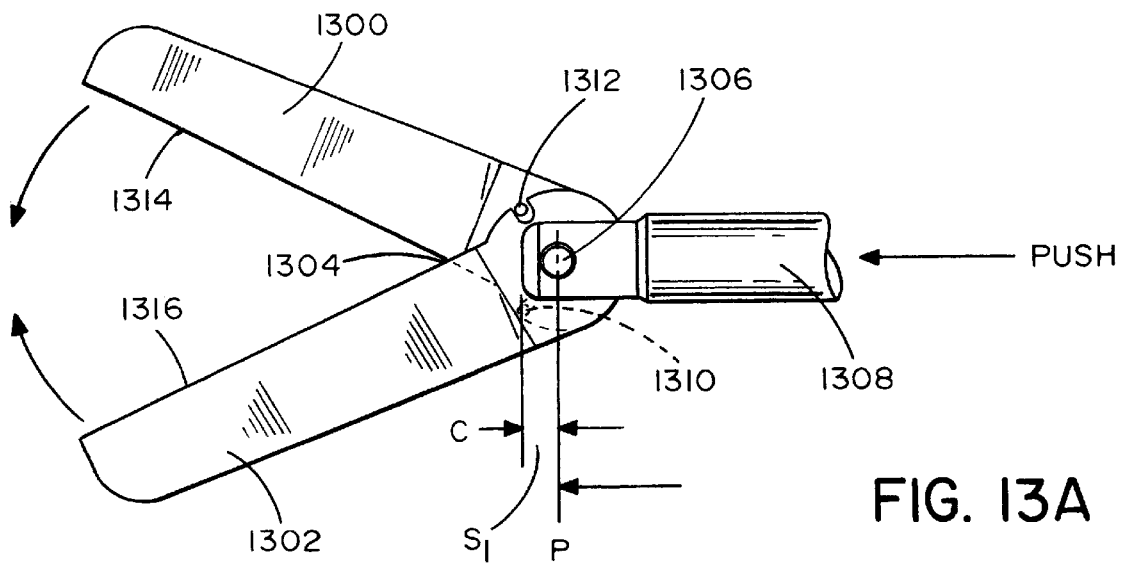
FIGS. 13A, 13B and 13C are side views of a scissors-type set of end effector elements in wide-open, partially-closed, and completely-closed positions, respectively, in a push-operation arrangement.

FIG. 13A is a counterpart to FIG. 12A but for a "pushing configuration", in which inner element 1308 is pushed by user operation of handle element 104 to operatively move end effector scissors elements 1300, 1302. In the wide-open disposition between end effector scissors elements 1300, 1302 per FIG. 13A, the tissue-intersection point 1304 between respective sharp edges 1314 and 1316 will be closest to the center of pin 1306 which, then, will be separated from axis "C" passing through the center of cam pins 1310, 1312 by a separation "$s_1$".

Figure 13B:
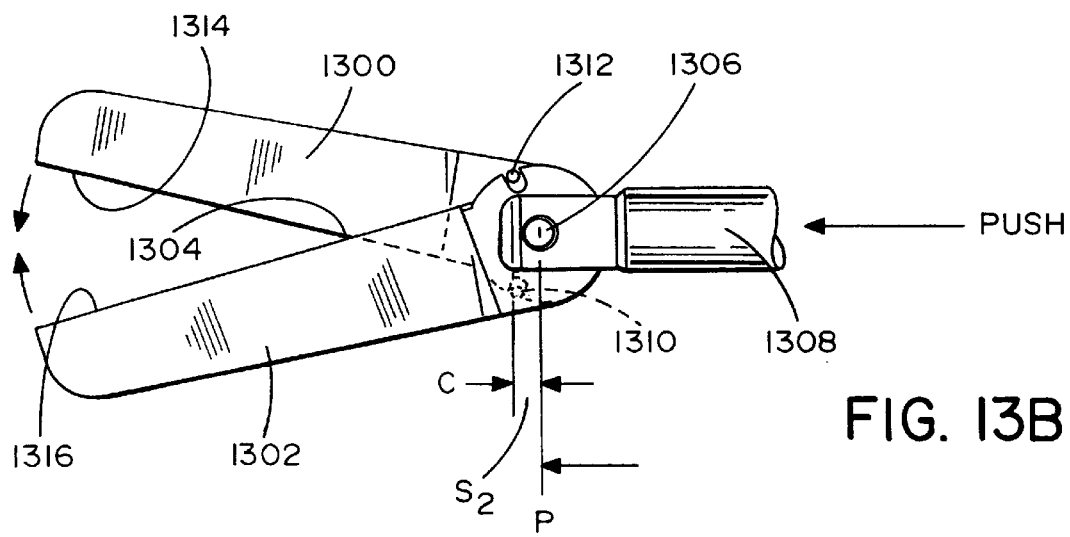
Figure 13C:
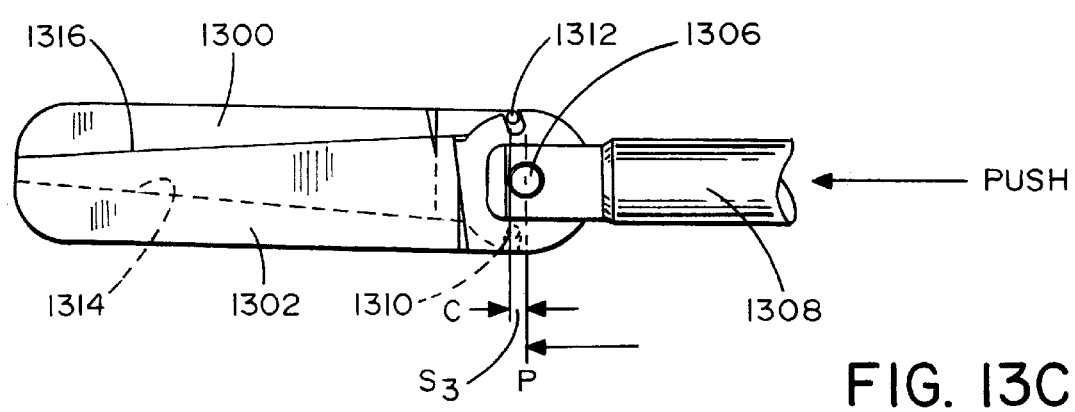

Upon the application of a pushing force on inner element 1308, pin 1306 will move forward relative to cam pins 1310, 1312 while tissue-intersection point 1304 also moves forward significantly with respect to pin 1306. The separation in the intermediate configuration shown in FIG. 13B between axis "C" passing the centers of cam pins 1313, 1312 and axis "P" passing through the center of pin 1306, is "$s_2$".

Finally, when the end effector scissors elements have rotated as much as possible under the action of the pushing force applied by the user to inner element 1308, pin 1306 will be at its closest separation relative to cam pins 1310, 1312, at a separation "$s_3$". End effector scissors elements 1300 and 1302 will then be in their "closed" position, and it is in this position that the instrument likely will be inserted through the cannula into the patient's body.

Reverse movement, i.e., the assertion of a pulling force on inner element 1308 relative to cam pins 1310, 1312, will cause the end effector scissors elements to rotate apart. Such a pulling force may be provided by a small spring acting on handle elements 110, 112, much as in small clippers, and the like. See FIG. 21C for an exemplary spring disposition.

FIGS. 14A and 14B relate to yet another variation of the invention, namely a pull-configuration with end effector grasping elements 1400, 1402 having tissue-contacting, non-slip, surface portions 1404, 1406 similar to those of the embodiment illustrated in FIGS. 11A, 11B. Note, however, that the embodiment per FIGS. 11A, 11B has cutouts 1116, 1118 opening on the same side as the force-applying sides of the respective end effector grasping elements 1100, 1102 in a "push configuration". By contrast, cutouts 1416, 1418 of end effector grasping elements 1400, 1402 in FIGS. 14A, 14B open on opposite sides relative to the non-slip surface portions 1404, 1406 in a "pull configuration". Yet another distinction between these two embodiments being compared is that the cutouts 1416, 1418 have respective longitudinal axes A—A and A'—A' which are not perpendicular to the lines corresponding to the non-slip grasping surface portions 1404, 1406, respectively. Having the cutouts oriented in this manner, with their respective longitudinal axes passing through the center of through-apertures 1412, 1414, provides improved leverage as discussed further below.

FIGS. 15A–15C relate to a "pull configuration" instrument with only one end effector element 1500 shown for simplicity. Such an end effector element could be one of the above-discussed grasping types or, in the alternative, could be a sawblade element which the user could dispose at a selected angle, as exemplified by "$\beta_1$", "$\beta_2$", or "$\beta_3$", which respect to the longitudinal axis of the inner element 400 and the outer tubular element 102.

FIGS. 16A and 16B illustrate yet another embodiment incorporating a pair of cooperating end effector grasping elements in a "pull configuration". This embodiment differs from the other "pull configuration" embodiments per FIGS. 7A–10B in that through-apertures in the force-receiving portions of the end effector grasping elements are replaced by radial cutouts 1650, 1652 which simultaneously engage with force-applying pin 1608. End effector grasping elements 1600, 1602 also contain cutouts 1616, 1618 which respectively engage with cam pins 516 (not shown) and 518 as best seen in FIG. 16B. In other words, the same outer tubular element 102 and inner element 400 may be employed in this embodiment as in the other "pull configuration" embodiments.

To assemble end effector grasping elements 1600, 1602 to the rest of the structure, the user must slide force-applying pin 1608 into each of radial slots 1650, 1652 simultaneously until slots 1616 and 1618 can be engaged with corresponding cam pins 516, 518. Note that the force-receiving portions of end effector grasping elements 1600, 1602 are each just a little less than one-half of the width of cleft 1610 in inner element 400. Also, note that the lengths of cam pins 516 and 518 cannot be more than the respective thicknesses of the force-receiving portions of end effector grasping elements 1600, 1602. This is necessary, as would be readily appreciated by persons of ordinary skill in the mechanical arts, for these components to be able to function as intended and as described above.

Numerous manufacturing techniques are available to ensure proper dimensioning of the above-discussed elements, and any of these may be employed as deemed appropriate. It may be possible to employ a stiff, light, relatively inexpensive plastics material for tubular element 102 or the handle elements. Force-applying pins such as 508 or 1608, for strength, probably are best made of a metal. The cooperating end effector elements may be made of hardened steel if they are to be provided sharp cutting edges, of a relatively light alloy if intended to perform only grasping functions, or of relatively light-weight plastics material or fiber-plastics composites. The exact choice of materials is not critical and is, in fact, very wide. Even exotic materials such as ceramics, metal/plastics or metal/ceramics combinations or the like may be considered for particular applications.

FIGS. 17A–17C show another variation, in which an exemplary end effector element 1700 has a force-receiving portion 1702 provided with a radial blind cutout 1704 for engaging with force-applying pin 508. End effector element 1700 is also provided with a forwardly inclined blind cutout 1706 for slidingly and rotatingly engaging with a corresponding cam pin 1708 cantilevered across just under one-half the width of the cleft formed at the distal end of tubular element 102.

Note that for convenience of illustration cam pin 1708 is shown as having a relatively small diameter compared with the width of corresponding cutout 1706 in FIGS. 17B and 17C. In practice, the tolerances between these two should be kept relatively small. Furthermore, to ensure strength, each cam pin such as 1708 is preferably provided with a small smooth radius at its base. The exact manner in which a structure is obtained is not considered critical.

As will be appreciated with reference to FIGS. 17B and 17C, a user-applied pull force acting on inner element 400 will cause it to retract within outer tubular element 102. Interactions among force-applying pin 508, cam pin 1708, and corresponding blind cutouts 1704 and 1706 will cause movement of end effector element 1700 at the distal end of the instrument. The other aspects of the structure and/or use and function considered to be generally comprehended in the previous discussion.

Persons of ordinary skill in the art will of course appreciate that if radial cutout 1704 were located so that its open end was on the same side as the force-applying surface portion 1710 of end effector element 1700, the instrument would be of the "push configuration".

FIGS. 18A and 18B show yet another embodiment, one which permits very quick disengagement of end effector grasping elements 1800, 1802 from outer tubular element 102 and inner element 400. In this embodiment, force-receiving portions 1804, 1806 of end effector grasping elements 1800, 1802 are each provided with only one radially inward cutout 1808, 1810, respectively. These cutouts are sized to be able to be fit to both force-applying pin 1812 and cam pins (only one shown per FIG. 18B) such as 1816.

In assembling these elements for useful operation, the user must first retract inner element 400 into outer tubular element 102 past cam pins such as 1816. The two end effector grasping elements 1800, 1802 must then be placed with their respective force-receiving portions 1804, 1806 adjacent to each other, with cutout 1810 receiving cam pin 1816 and cutout 1808 slid over to receive a corresponding cam pin (not shown). By operating handle mechanism 104, the user must then push inner element 400 forward, with end effector grasping elements 1800, 1802 rotated relative to their corresponding cam pins until cutouts 1808 and 1810 both simultaneously engage with force-applying pin 1812 until it reaches their blind ends. Further forward movement of inner element 400 will cause end effector grasping elements 1800, 1802 to swing away from each other in rotation about force-applying pin 1808. Furthermore, and this is important, end effector grasping elements 1800, 1802 will be securely retained by co-action of force-applying pin 1812 and the cooperating cam pins received within the cutouts 1808, 1810. The device as illustrated in FIGS. 18A, 18B is thus intended to be of the "push configuration" type.

A user having employed a particular pair of end effector elements such as 1800, 1802, may wish to replace them with another set. He must retract inner element 400 to permit disengagement of force-applying pin 1812 from both of cutouts 1808 and 1810. Force-receiving portions 1804, 1806 may then be slid outwardly to release them from respective engagements with corresponding cam pins such as 1816. The next chosen pair of corresponding end effector elements may then be placed and engaged as described above.

Figures 19A, 19B:
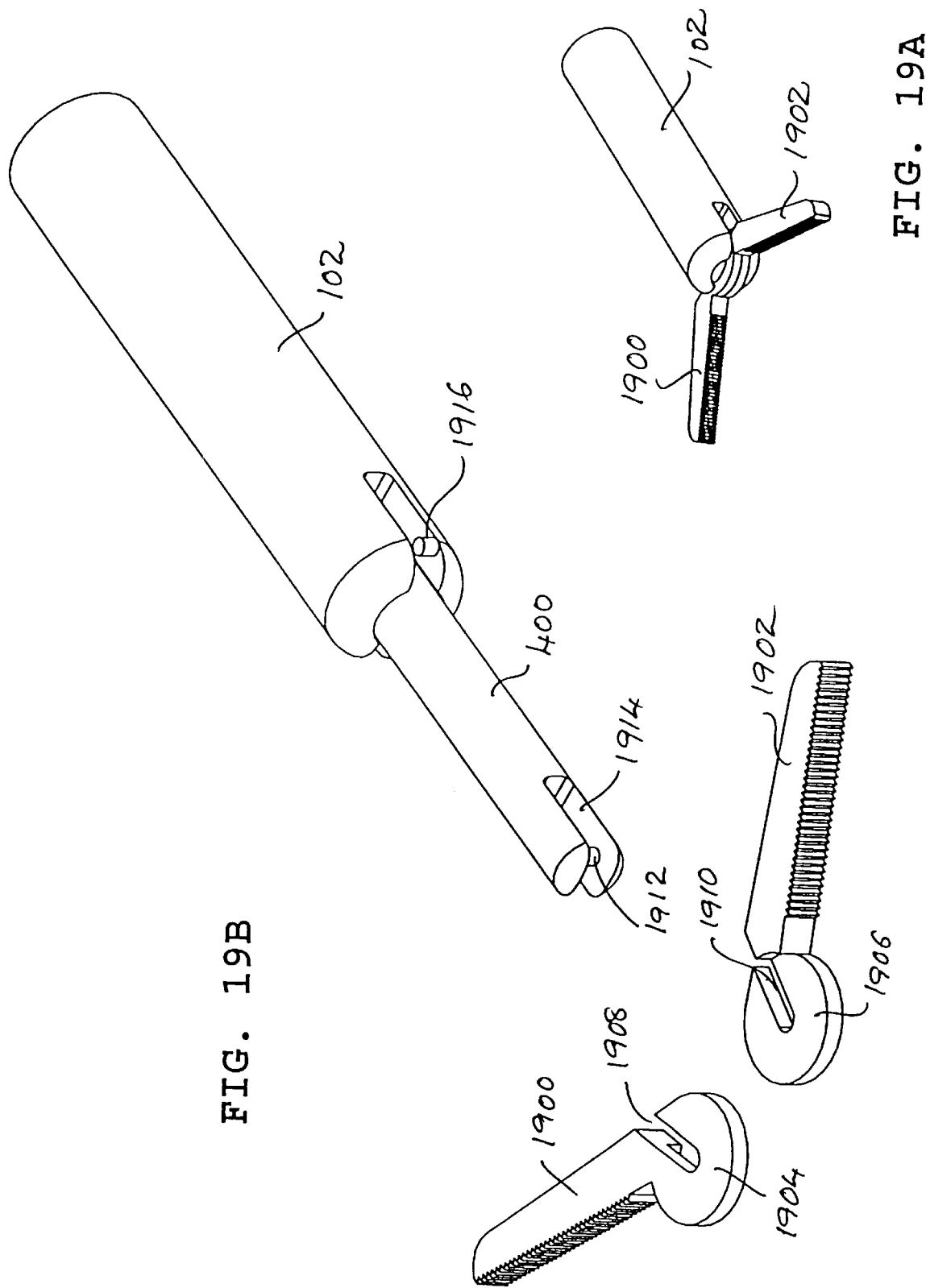
FIG. 19A is a perspective view.
FIG. 19B is an exploded view, of an elongate clamp arrangement in which each end effector element is provided with a forwardly inclined groove which simultaneously engages with a drive pin provided in a rod element and a cantilever pin provided in an outer tubular element, in a pull-operation arrangement.

FIGS. 19A and 19B illustrate a "pull configuration" variant comparable to the embodiment illustrated in FIGS. 18 and 18B. The embodiment per FIGS. 19A and 19B comprises the standard outer tubular element 102, the standard inner element 400 slidingly contained therein, a force-applying pin 1912 fitted transversely to bridge cleft 1914 in the distal end of inner element 400, and a pair of cooperating end effector grasping elements 1900, 1902 with force-receiving portions 1904, 1906 having thicknesses slightly less than one-half the transverse dimension of cleft 1914 and corresponding radial blind cutouts 1908, 1910. The embodiment of FIGS. 19A, 19B is of a "pull configuration", hence cutouts 1908, 1910 have their respective openings on opposite sides of the force-applying, non-slip, portions of end effector grasping elements 1900, 1902.

Assembly of the cooperating elements per FIGS. 19A, 19B for operational use is simple. End effector grasping elements 1900, 1902 should be put together with their respective radial cutouts 1908, 1910 aligned with each other and together slipped into cleft 1914 to receive force-applying pin 1912. Inner element 400 then should be retracted within outer tubular element 102 and end effector grasping elements 1900, 1902 individually rotated until they engage with respective cam pins. Further retraction of inner element 400 will cause end effector grasping elements 1900, 1902 to rotate their force-applying, non-slip surface portions toward each other to effect a grasping action on any tissue located therebetween. Such rotation will securely retain the end-effector elements in mutual engagement with both the force-applying pin 1912 (and thus inner element 400) and the respective cooperating cam pins such as 1916 (and thus with tubular outer element 102). Operation of this embodiment is otherwise the same as for any of the other "push configuration" embodiments discussed above, and hence will not be discussed further.

FIG. 20A is a side view of a "push configuration" instrument 2000 having an elongate outer tubular element 2002 with a pair cooperating end effector elements 2004, 2006 at the distal end thereof. Outer tubular element 2002 at its proximal end is provided with a head 2010 having a non-slip configured outer surface with which a user may determine its angular orientation relative to first handle element 2012.

A second handle element 2014 is pivotably engaged with first handle element 2012 and, simultaneously, is movably attached to the proximal end 2016 of an elongate inner element 2018, as best seen in the enlarged view in FIG. 20B. Note that the pivoting engagement between handle elements 2012 and 2014 is provided by a pivot arrangement 2020 of known type which is located on an opposite side of the longitudinal axis Z—Z of outer tubular element 2002 with respect to the loops in handle elements 2012, 2014. Accordingly, when handle elements 2012, 2014 are pressed towards each other handle element 2014 will rotate about pivot arrangement 2020 to push the proximal end 2016 of inner element 2018 forwardly and longitudinally within outer tubular element 2002.

FIG. 21A shows a "pull configuration" type of instrument 2100 which comprises elongate outer tubular element 2102, cooperating end effector elements 2104, 2106, enlarged head 2110 at the proximal end of tubular element 2102, and cooperating handle elements 2112, 2114. As best seen in the enlarged view in FIG. 21B, handle element 2114 pivotably engages with handle element 2112 at a pivot 2120 pivoted between the longitudinal axis of outer tubular element 2102 and the closed loops of handle elements 2112 and 2114.

As described earlier with respect to FIG. 3, the distal end of the handle element 2114 (which has the small closed loop to receive the user's thumb) contains a socket shaped and sized to movably but closely receive therein the enlarged distal proximal end 2122 of inner element 2118. With this arrangement, when the user presses handle elements 2112, 2114 towards each other at their respective loop portions, pivoting engagements will cause the distal enlarged end portion of 2122 of inner element 2118 to be retracted backward along the length of outer tubular element 2102, hence the instrument is one of the "pull configuration".

FIG. 21C more clearly shows portions of handle elements 2112 and 2114 close to a pivot pin 2130 provided in a bracket 2132 of handle element 2114. Accommodation for the distal end of bracket 2132 and pivot pin 2130 may be made by forming recess 2134 and otherwise shaping element 2112 in any known manner. The exact details of this structure are not critical so long as a well-fitted pivoting action is obtained.

Furthermore, to ensure against inadvertent or accidental movement of inner element 2118 within outer tubular element 2102 sufficient to cause possible disengagement of end effector elements from the instrument, a conventional detent mechanism 2136 of any known type may be formed and/or otherwise provided. The sole purpose of such a detent mechanism is to alert the user that the handle elements have reached a pivotal relationship such that further motion between them will cause the end effector elements to become disengaged. The detent could be one which provides an abruptly increased resistance to further motion of the cooperating handle elements, a clicking sound, or a noticeable discontinuity in the feel of the instrument in the user's hands. The exact details of the arrangement are not critical and adaptations of any known detent mechanisms for such purposes should be considered acceptable.

FIG. 21C also generally indicates how an exemplary helical spring 2128 may be fitted between cooperating handle elements 2112 and 2114 to bias them apart until overcome by a force deliberately applied by the user.

Figure 22A:
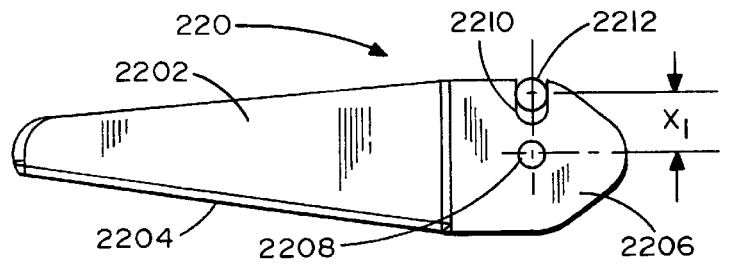
FIG. 22A is a side view of a pull-operation type of scissors blade provided with a through-aperture for passage of a pull-rod pin therethrough and a short groove extending radially inward toward the center of that through-aperture.

FIG. 22A illustrates in side view an end effector scissors element 2200 having a force-applying portion 2202 provided with a cutting edge 2204 and force-receiving portion 2206 which has a through-aperture 2208 to receive a force-applying pin bridging a cleft in the distal end of an inner element. The force-receiving portion 2206 is also provided with a radially inward cutout 2210 having an opening on the opposite side of cutting edge 2204 and sized to receive therein a cam pin 2212. What is important to note is that cutout 2210 has a longitudinal axis aligned with the center of aperture 2208 and that at closest approach the radial separation between the centers of cam pins 2212 and through-aperture 2208 is "$x_1$".

Figure 22B:
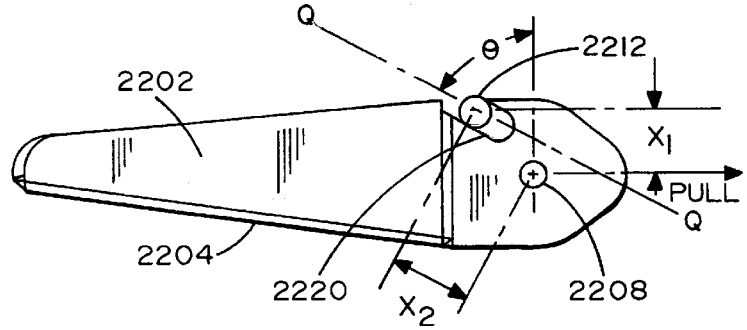
FIG. 22B is a view of an embodiment in which the scissors-type end effector element is provided with a through-aperture for receiving a pull-rod pin and a forwardly inclined groove for engaging with the cantilevered pin of an outer tube element.

FIG. 22B shows a similar end effector scissors element which differs from that shown in FIG. 22A in only one regard, i.e., that the force-receiving portion 2206 thereof contains a blind cutout 2220 which has a longitudinal axis of Q—Q offset from the center of through-aperture 2208. Furthermore, axis Q—Q is inclined and is not perpendicular to the line along which a force would be applied to a force-applying pin passed into through-aperture 2208. With this arrangement, even if the transverse separation between the centers of cam pins 2212 and the center of through-aperture 2208 is still "$x_1$", the radial separation between them is a larger distance "$x_2$". As persons of ordinary skill in the mechanical arts will appreciate, such a geometric difference between the structure illustrated in FIGS. 22A and 22B results in the latter having a greater mechanical advantage of end effector element 2202 about the force-applying cam pin located in through-aperture 2208. Such an arrangement may permit more precise control and allow more powerful incision making with the use of the end effector scissors element 2202.

In short, this invention permits many variations by which appropriately selected end effector elements can be operated in different ways. It therefore constitutes a modular system in which modular sets of end effector elements may be made available to the user for quick engagement with a single medical instrument to perform a variety of surgical procedures.

Figure 23:
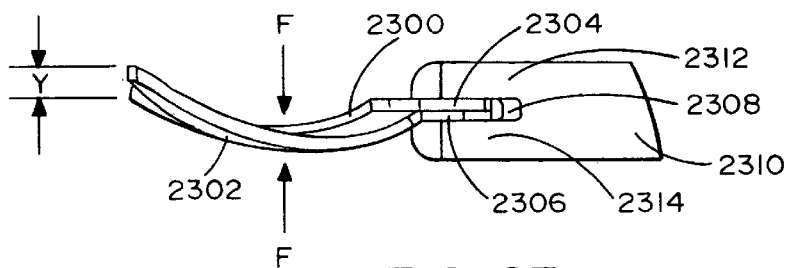
FIG. 23 is a plan view to explain a sprung engagement of a pair of scissors-type end effector elements in the clevis of an outer tube element.

FIG. 23 is a view looking down on a pair of end effector scissors elements 2300, 2302 cooperatively engaged in an instrument according to the preferred embodiment. To ensure that the respective sharp cutting edges of these two end effector scissors elements remain firmly pressed to each other at all times, it is preferable to have them slightly curved or twisted towards each other at least along their cutting edges. This is generally indicated by the letter "y". Actually, any such curve or twisting of end effector scissors elements 2300, 2302 towards each other will require the application of a transverse force "F" therebetween as indicated in FIG. 23. By selection of suitable dimensions for the thicknesses of the force-receiving portions 2304, 2306 of end effector scissors elements 2300, 2302 and of cleft 2308 in the distal end of outer tubular element 2310, the two parallel arms 2312, 2314 can be employed as leaf springs holding the end effector scissors elements 2300, 2302 forcibly to each other as they rotate. The required dimensioning precision is currently available, and if the outer tubular element 2310 is made of a sufficiently elastic/resilient stiff material the desired effect can be readily obtained at affordable cost.

It is emphasized again that the exact details of structure, choice of materials, and dimensions will depend upon the particular application at hand and that persons in the ordinary skill in the art can be readily expected to select these as most appropriate in light of the intended use of the instrument. What is important, however, is that the force-receiving portions such as 2206, 1108 be sufficiently wide so they press to corresponding force-receiving portions of the cooperating end effector element and are simultaneously pressed towards each other by the immediately adjacent surfaces defining cleft 2308. In other words, if arms 2312, 2314 are to effectively press force-receiving portions 2304, 2306 to each other firmly, contact therebetween must be made at as large a distance away from the axis of the outer tubular element as possible. The present invention permits maximization of this feature.

Figure 24A:
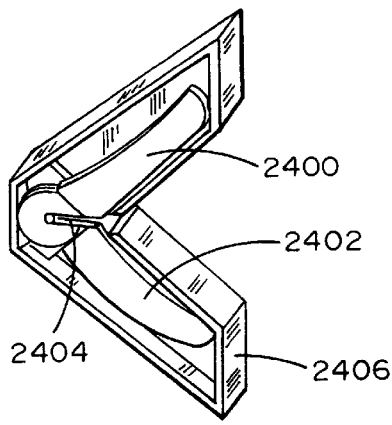
FIGS. 24A and 24B are both perspective views of a V-profile storage cartridge containing a pair of suitably aligned end effector elements each of which has a single radial groove for simultaneous engagement with a rod pin and a cantilever pin of an outer tubular element in a pull-operation version of this invention per FIGS. 19A and 19B.
Figure 24B:
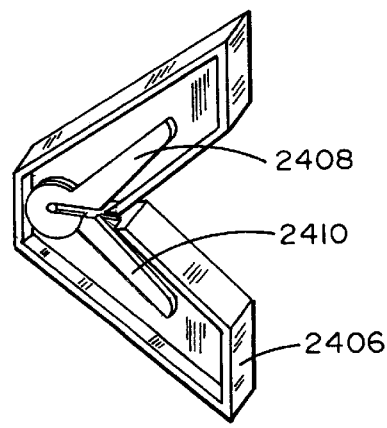

For embodiments which permit quick change of end effector elements as discussed above, storing differently shaped end effector elements by pairs, in sterile-packaging and in proper alignment, is highly desirable to provide a versatile modular system. FIG. 24A shows a first pair of end effector elements 2400, 2402 with their respective single cutouts (for a "pull configuration") totally aligned with each other at 2404 in a pressed-fitted arrangement within a generally "V-shaped" retention element 2406. FIG. 24B shows how an opposite side of retention element 2406 may contain a similar recess or space to locate, in press-fit or other manner, a second set of end effector elements 2408, 2410 also aligned for quick engagement. Retention element 2406, after installation of the exemplary two pairs of cooperating end effector elements, may be enclosed in a contamination-excluding sealed container made, of a heat-sealed vacuum-packed plastic or the like. With such an arrangement, once a surgeon commences a surgical operation/procedure, he may request his assistants to provide him with a selected pair of end effector elements by name, e.g., a "scissors" pair 2400, 2402 or a "clamp" pair 2408, 2410. The assistant may then open the vacuum-sealed pouch and hold it so that the surgeon may remove used end effector elements from the instrument and extend the distal end of the inner element outwardly of the surgical instrument so that the force-applying pin is received within the aligned cutouts 2404. With a slight twist, the new end effector elements may be released from their force-fit location within element 2406. Then, with suitable operation of the handle elements as described above, the surgeon may securely engage the newly-selected pair of end effector elements for immediate use.

As will be readily appreciated, end effector elements may be made of a suitable metal, e.g., stainless steel or the like, may be sterilized in autoclaves, ultraviolet sterilization chambers, or otherwise, located within appropriate container elements 2406, and sealed against contamination for future use.

The above description discloses related embodiments and the manner of their use according to the present invention, and is not intended to be limiting. The present invention may be modified in obvious manner by persons of ordinary skill in the art, and its scope is defined solely by the claims appended below.

What is claimed is:

1. An apparatus, comprising:
   an elongate outer tubular element having a proximal end and a distal end formed to have a first cleft, the first cleft having a first cleft orientation defining a first plane;
   an elongate inner element having a proximal end and a distal end formed to have a second cleft, the second cleft having a second cleft orientation defining a second plane;
   a mechanism for controllably moving the inner element longitudinally within the tubular element;
   a force-application pin mounted to the inner element to bridge the second cleft;
   a pair of parallel cantilevered cam pins, each of the cantilevered cam pins having an elongate axis, the pair of cam pins being mounted on opposite sides of a central axis of the tubular element inside the first cleft and wherein the elongate axis of each cam pin is oriented in a direction transverse to the first plane and transverse to the second plane; and a pair of cooperating end effector elements, each having a force-receiving portion and a force-applying portion, each force-receiving portion being formed to pivotally engage with the force-application pin and to simultaneously engage with a respective one of the cam pins, so that relative longitudinal motion between the tubular element and the inner element when in a first direction causes forcible rotations of the end effector elements about the force-application pin to drive the force-applying portions toward each other and when in a second direction causes opposite forcible rotations of the end effector elements about the force-application pin to drive the force-applying portions apart.

2. The apparatus according to claim 1, wherein:
the force-application pin is removably fitted to the inner element.

3. The apparatus according to claim 1, wherein:
the force-receiving portion of each end effector element is provided with a through-aperture sized for receiving the force-application pin therein and is also provided with a blind cutout sized to receive therein the corresponding cam pin.

4. The apparatus according to claim 3, wherein:
each end effector element has a corresponding force-application side, with the force-application sides of the pair of end effector elements facing each other, and the cutout in each end effector element is oriented to have an open end facing away from the force-application side and a closed end between the open end and the through-aperture, whereby a pushing force applied to the proximal end of the inner element provides motion thereof relative to the tubular element in said first direction.

5. The apparatus according to claim 4, wherein:
the cutout in each of the end effector elements has an elongate axis which extends through a center of the corresponding through-aperture.

6. The apparatus of claim 5, wherein the cutout in each of the end effector elements engages with a respective one of the cam pins within the cutout.

7. The apparatus of claim 6, wherein the cutout in each of the end effector elements slidably engages with a respective one of the cam pins within the cutout in a direction along the elongate axis of the cutout.

8. The apparatus of claim 7, wherein the forcible rotations of the end effector elements about the force-application pin provides a mechanical advantage upon each cam pin.

9. The apparatus according to claim 4, wherein:
the cutout in each of the end effector elements has a longitudinal axis offset relative to a center of the corresponding through-aperture.

10. The apparatus according to claim 3, wherein:
each end effector element has a corresponding force-application side, with the force-application sides of the end effector elements facing each other, and the cutout in each end effector element is oriented to have an open end facing toward the corresponding force-application side and a closed end between the open end and the through-aperture, whereby a pulling force applied by said mechanism to the proximal end of the inner element provides motion thereof relative to the tubular element in said first direction.

11. The apparatus according to claim 10, wherein:
the cutout in each end effector element has a longitudinal axis which extends through a center of the corresponding through-aperture.

12. The apparatus according to claim 10, wherein:
the cutout in each end effector element has a longitudinal axis offset relative to a center of the corresponding through-aperture.

13. The apparatus according to claim 1, wherein:
the force-receiving portion of each end effector element is provided with a single blind cutout formed to receive therein both the force-application pin and the corresponding cam pin.

14. The apparatus according to claim 13, wherein:
each end effector element has a corresponding force-application side, with the force-application sides of the pair of end effector elements facing each other, and the cutout in each end effector element is oriented to have an open end facing away from the force-application side, whereby a pushing force applied by said mechanism to the proximal end of the inner element provides motion thereof relative to the tubular element in said first direction.

15. The apparatus according to claim 13, wherein:
each end effector element has a corresponding force-application side, with the force-application side of the pair of effector elements facing each other, and the cutout in each end effector elements is oriented to have an open end facing towards the force-application side, whereby a pulling force applied by said mechanism to the proximal end of the inner element provides motion thereof relative to the tubular element in said first direction.

16. The apparatus according to claim 13, wherein:
additional pairs of cooperating end effector elements are respectively retained in contamination-resistant modular storage containers with the respective single blind cutouts mutually aligned to facilitate selective engagement of said additional end effector elements to the tubular and inner elements.

17. The apparatus according to claim 13, wherein:
the force-receiving portion of each end effector element comprises a first surface facing to a corresponding first surface of the other cooperating end effector element;

the force-receiving portion of each end effector element has a second surface disposed to make contact with a corresponding surface of the first cleft of the tubular element; and the force-receiving portions of the cooperating end effector elements and the first cleft are sized to provide a close fit during use of the apparatus, such that any tendency of the force-applying portions of the cooperating end effector elements to deflect laterally will be resisted by the tubular element at said first cleft.

18. The according to claim 17, wherein:
said mechanism for moving the inner element relative to the tubular element comprises a first handle element detachably connected to the proximal end of the tubular element, and a second handle element detachably connected to the proximal end of the inner element;

the tubular element is rotatable relative to the first handle element, and the inner element is correspondingly rotatable relative to the second handle element;

the first and second handle elements pivot relative to each other about a pivot axis; and said mechanism further comprises a positional detent disposed to inform a user of the apparatus when additional pivoting movement of the first handle element relative to the second handle element to cause relative movement of the tubular element relative to the inner element will move the end effector elements into in a position where the end effector elements may be disengaged from the corresponding cam pins.

19. The apparatus according to claim 18, wherein:

the pivot axis is disposed such that pivoting movement between the first handle element and second handle element will cause the second handle element to apply a pulling force to the proximal end of the inner element.

20. The apparatus according to claim 18, wherein:

the pivot axis is disposed such that pivoting movement between the first handle element and second handle element will cause the second handle element to apply a pushing force to the proximal end of the inner element.

21. An apparatus according to claim 1, wherein:

the end effector elements consist of a pair of scissors blades which have respective sharp edges maintained to be forcibly pressed to each other to cooperatively provide a shearing action.

22. The apparatus according to claim 1, wherein:

the cooperating end effector elements have respective force-applying portions facing to each other to provide a grasping action therebetween when relative longitudinal motion between the tubular element and the inner element occurs in said first direction.

23. The apparatus according to claim 22, wherein:

each force-applying portion has a non-slip surface disposed to face a corresponding non-slip surface of the other end effector element.

24. The apparatus according to claim 23, wherein:

the non-slip surfaces of the end effector elements are matchingly shaped.

25. The apparatus according to claim 24, wherein:

the matching shape is substantially curved.

26. An apparatus according to claim 1, wherein:

said mechanism for moving the inner element relative to the tubular element comprises
a first handle element, detachably connected to the proximal end of the tubular element, and
a second handle element, detachably connected to the proximal end of the inner element.

27. The apparatus according to claim 26, wherein:

the tubular element is rotatable relative to the first handle element, and the inner element is correspondingly rotatable relative to the second handle element.

28. The apparatus according to claim 26, wherein:

the first and second handle elements pivot relative to each other about a pivot axis, and said mechanism further comprises a positional detent disposed to inform a user of the apparatus when additional pivoting movement of the first handle element relative to the second handle element to cause relative movement of the tubular element relative to the inner element will move the end effector elements into a position where the end effector elements may be disengaged from the corresponding cam pins.

29. The apparatus according to claim 28, wherein:

the pivot axis is disposed such that pivoting movement between the first handle element and second handle element will cause the second handle element to apply a pulling force to the proximal end of the inner element.

30. The apparatus according to claim 28, wherein:

the pivot axis is disposed such that pivoting movement between the first handle element and second handle element will cause the second handle element to apply a pushing force to the proximal end of the inner element.

31. The apparatus according to claim 1, wherein:

the force-receiving portion of each end effector element comprises a first surface facing to a corresponding first surface of the other cooperating end effector element, and the force-receiving portion of each end effector element has a second surface disposed to make contact with a corresponding surface of the first cleft of the tubular element.

32. The apparatus according to claim 31, wherein:

the force-receiving portions of the cooperating end effector elements and the first cleft are sized to provide a close fit during use of the apparatus, such that any tendency of the force-applying portions of the cooperating end effector elements to deflect laterally will be resisted by the tubular element at said first cleft.

33. The apparatus according to claim 1, wherein:

at least one of the tubular element, the inner element, the first handle element and the second handle element comprises a plastics material.

34. The apparatus of claim 1, wherein the forcible rotations of the cooperating end effector elements occur in a rotation plane, and wherein the forcible rotations of the cooperating end effector elements produces a pair of forces oppositely extending from the cooperating end effector elements, each of the pair of forces being oriented in a direction transverse to the rotation plane.

35. The apparatus of claim 34, wherein the first cleft comprises a pair of parallel arms, wherein the pair of parallel arms retains the pair of cooperating end effector elements, each of the pair of parallel arms being springably flexible, wherein the pair of parallel arms are springably biased opposite the direction of each of the pair of forces.

36. The apparatus of claim 1, wherein each of the cooperating end effector elements includes a cutout, and wherein each of the cooperating end effector elements engages with a respective one of the cam pins within the cutout.

37. The apparatus of claim 36, wherein each cutout includes at least one edge, and wherein each of the cooperating end effector elements slidably cams upon the at least one edge.

38. The apparatus of claim 37, wherein the slidable camming of each of the cooperating end effector elements upon the cam pins provides a mechanical advantage throughout the forcible rotations of the end effector elements about the force-application pin.

39. The apparatus of claim 1, wherein each of the pair of cam pins has a cam pin length, wherein the first cleft has a width of opening, and wherein the cam pin length of each of the pair of cam pins is not more than one half the width of opening of the first cleft.

40. An improved hand-held surgical instrument comprising an elongate outer tubular element having a proximal end and a distal end, an elongate inner element disposed longitudinally within the tubular element and having a proximal end and a distal end, and a mechanism for controllably moving the inner element longitudinally within the tubular element to actuate a pair of cooperating end effector elements which engage with both the tubular element and the inner element, wherein the improvement comprises:

a first cleft formed in the distal end of the tubular element, the first cleft having a first cleft orientation defining a first plane;

a second cleft formed in the distal end of the inner element, the second cleft having a second cleft orientation defining a second plane;

a force-application pin mounted to the inner element to bridge the second cleft therein; and a pair of parallel cantilevered cam pins, each of the cantilevered cam pins having an elongate axis, the pair of cam pins being mounted on opposite sides of a central axis of the tubular element inside the first cleft, wherein the elongate axis of each of the cam pins is oriented in a direction transverse to the first plane and transverse to the second plane;

wherein each end effector element is provided with a force-receiving portion and a force-applying portion, each force-receiving portion being formed to pivotally engage with the force-application pin and to simultaneously engage with a respective cam pin, so that longitudinal motion between the tubular element and the inner element when in a first direction causes forcible rotations of the end effector elements about the force-application pin to drive the force-application portions toward each other and when in a second direction causes opposite forcible rotations of the end effector elements about the force-application pin to drive the force-applying portions apart.

41. The improved apparatus according to claim 40, wherein:

the force-receiving portion of each end effector element is provided with a through-aperture sized for receiving the force-application pin therein and is also provided with a blind cutout sized to receive therein the corresponding cam pin.

42. The improved apparatus according to claim 40, wherein:

each end effector element has a corresponding force-application side, with the force-application sides of the pair of end effector elements facing each other; and the cutout in each end effector element is oriented to have an open end facing away from the force-application side and a closed end between the open end and the through-aperture, whereby a pushing force applied to the proximal end of the inner element provides motion thereof relative to the tubular element in said first direction.

43. The improved apparatus according to claim 42, wherein:

each end effector element has a corresponding force-application side, with the force-application sides of the end effector elements facing each other; and the cutout in each end effector element is oriented to have an open end facing toward the corresponding force-application side and a closed end between the open end and the through-aperture, whereby a pulling force applied by said mechanism to the proximal end of the inner element provides motion thereof relative to the tubular element in said first direction.

44. The improved apparatus according to claim 40, wherein:

the force-receiving portion of each end effector element is provided with a single blind cutout formed to receive therein both the force-application pin and the corresponding cam pin.

45. The improved apparatus according to claim 44, wherein:

additional pairs of cooperating end effector elements are respectively retained in contamination-resistant modular storage containers with the respective single blind cutouts mutually aligned to facilitate selective engagement of said additional end effector elements to the tubular and inner elements.

46. The apparatus of claim 44, wherein each of the pair of cam pins has a cam pin length, wherein the first cleft has a width of opening, and wherein the cam pin length of each of the pair of cam pins is not more than one half the width of opening of the first cleft.

47. The apparatus of claim 46, wherein the first cleft has an opening defined thereby, and wherein each of the pair of cam pins extends inwardly within the first cleft opening.

48. A method of mounting a pair of cooperating end effector elements to a hand-held surgical instrument which comprises an elongate outer tubular element having a proximal end and a distal end formed to have a first cleft, the first cleft having a first cleft orientation defining a first plane, an elongate inner element having a proximal end and a distal end formed to have a second cleft, and a mechanism for controllably moving the inner element longitudinally within the tubular element, the second cleft having a second cleft orientation defining a second plane, comprising the steps of:

providing a force-application pin mounted to the inner element so as to bridge the second cleft therein;

providing a pair of parallel cantilevered cam pins, each of the cantilevered cam pins having an elongate axis, the pair of cam pins being mounted on opposite sides of a central axis of the tubular element inside the first cleft, wherein the elongate axis of each of the cam pins is oriented in a direction transverse to the first plane and transverse to the second plane;

providing a pair of cooperating end effector elements each having a force-receiving portion and a force-applying portion, each force-receiving portion being formed to have a single blind cutout formed to receive therein both the force-application pin and a corresponding cam pin, each force-receiving portion also being formed to pivotally engage with the force-application pin and to simultaneously engage with a respective cam pin so that relative longitudinal motion between the tubular element and the inner element when in a first direction causes forcible rotations of the end effector elements about the force-application pin to drive the force-applying portions toward each other and when in a second direction causes opposite forcible rotations of the end effector elements about the force-application pin to drive the force-applying portions apart.

49. The method according to claim 48 comprising the further steps of:

moving the inner element relative to the tubular element to a first relative position in which the pair of end effector elements can be slidably removed and a replacement pair of end effector elements slidably fitted simultaneously to the tubular element and the inner element, and thereafter moving the inner element longitudinally of the tubular element to rotate the mounted pair of end effector elements as the inner element and the tubular element are moved further relative to each other.

* * * * *